US011701335B2

United States Patent
Reiner et al.

(10) Patent No.: US 11,701,335 B2
(45) Date of Patent: Jul. 18, 2023

(54) METHODS OF NORMALIZING AMINO ACID METABOLISM

(71) Applicant: APR Applied Pharma Research s.a., Balerna (CH)

(72) Inventors: Alberto Reiner, Como (IT); Giorgio Reiner, Como (IT)

(73) Assignee: APR Applied Pharma Research s.a., Balerna (CH)

( * ) Notice: Subject to any disclaimer, the term of this patent is extended or adjusted under 35 U.S.C. 154(b) by 0 days.

(21) Appl. No.: 16/543,437

(22) Filed: Aug. 16, 2019

(65) Prior Publication Data

US 2020/0069624 A1 Mar. 5, 2020

Related U.S. Application Data

(60) Provisional application No. 62/725,420, filed on Aug. 31, 2018.

(51) Int. Cl.
| | |
|---|---|
| *A61K 31/401* | (2006.01) |
| *A61P 3/08* | (2006.01) |
| *A61K 31/4172* | (2006.01) |
| *A61K 31/198* | (2006.01) |
| *A61K 31/197* | (2006.01) |
| *A61K 9/00* | (2006.01) |
| *A61P 3/02* | (2006.01) |
| *A61K 9/16* | (2006.01) |
| *A61K 9/50* | (2006.01) |
| *A61K 31/405* | (2006.01) |
| *A61K 45/06* | (2006.01) |

(52) U.S. Cl.
CPC .............. *A61K 31/198* (2013.01); *A61K 9/16* (2013.01); *A61K 9/5036* (2013.01); *A61K 9/5047* (2013.01); *A61K 31/197* (2013.01); *A61K 31/401* (2013.01); *A61K 31/405* (2013.01); *A61K 31/4172* (2013.01); *A61K 45/06* (2013.01); *A61P 3/02* (2018.01)

(58) Field of Classification Search
CPC ...... A61K 31/198; A61K 9/16; A61K 9/5036; A61K 9/5047; A61K 31/197; A61K 31/401; A61K 31/405; A61K 31/4172; A61K 45/06; A61P 3/02
See application file for complete search history.

(56) References Cited

U.S. PATENT DOCUMENTS

| | | | | |
|---|---|---|---|---|
| 5,026,721 | A | * | 6/1991 | Dudrick ............... A61K 31/195 514/396 |
| 10,500,180 | B2 | | 12/2019 | Reiner et al. |
| 2002/0004072 | A1 | * | 1/2002 | Thomas ............. A61K 31/4172 424/491 |
| 2004/0006140 | A1 | | 1/2004 | Kaesemeyer |
| 2004/0213838 | A1 | | 10/2004 | Mazer et al. |
| 2010/0009006 | A1 | | 1/2010 | Hill et al. |
| 2013/0251803 | A1 | * | 9/2013 | Cawello ............... A61K 31/165 424/474 |
| 2018/0185311 | A1 | | 7/2018 | Reiner |

FOREIGN PATENT DOCUMENTS

| | | |
|---|---|---|
| EP | 1774858 A1 | 4/2007 |
| GB | 1217365 A | 12/1970 |
| WO | WO-0067797 A1 | 11/2000 |
| WO | WO-2011043647 A1 | 4/2011 |
| WO | WO-2016112170 A1 | 7/2016 |
| WO | 2017/055997 A1 | 4/2017 |

OTHER PUBLICATIONS

Giovannini et al. (Journal of the American College of Nutrition, 33(2):103-110, 2014.*
Pasiakos et al., military Nutrition Division, US Army Research Institute, 2014.*
Weigel, et al.; Effects of Various Dietary Amino Acid Preparations for Phenylketonuric Patients On the Metabolic Profiles Along With Postprandial Insulin and Ghrelin Responses; Annals of Nutrition & Metabolism; 2007; 51:352-358.
Uhe, et al.; Amino Acid Levels Following Beef Protein and Amino Acid Supplement in Male Subjects; Asia Pacific J. Clin. Nutr. (1997) 6(3): 219-223.
Reltelseder, et al.; Whey and Casein Labeled With L-[1-13C] Leucine and Muscle Protein Synthesis: Effect of Resistance Exercise and Protein Ingestion; Am J. Physiol Endocrinol Metab 300: E231-E242, 2011.
Rubio et al.; Molecular Size Distribution Affects Portal Absorption Rate of Casein Amino Acids in Rats; Journal of Animal Physiology and Animal Nutrition 94 (2010) e145-e153.
Daly et al.; Inborn Errors of Metabolism: Glycomacropeptide in Children With Phenylketonuria: Does Its Phenylalanin Content Affect Blood Phenylalanine Control?; Journal of Human Nutrition and Dietetics; The British Dietetic Association Ltd.; 2017; 515-523.
Dangin et al.; The Digestion Rate of Protein is an Independent Regulating Factor of Postprandial Protein Retention; Am J Physiol Endocrinol Metab; 280: E340-E348, 2001.
Dioguardi, Francesco S.; Clinical Use of Amino Acids as Dietary Supplement: Pros and Cons; J. Cachexia Sarcopenia Muscle (2011) 2:75-80.
Gropper et al.; Effect of Simultaneous Ingestion of L-Amino Acids and Whole Protein On Plasma Amino Acid and Urea Nitrogen Concentrations in Humans; Journal of Parenteral and Enteral Nutrition; 1991 15: 48-53.

(Continued)

*Primary Examiner* — Alma Pipic

(74) *Attorney, Agent, or Firm* — Sterne, Kessler, Goldstein & Fox P.L.L.C.

(57) ABSTRACT

Methods of normalizing amino acid metabolism in subjects on restricted protein diets and supplemental amino acids, using specially formulated amino acids that mimic the absorption and metabolism of naturally occurring proteins, are described.

21 Claims, 18 Drawing Sheets

(56) References Cited

OTHER PUBLICATIONS

Donlon; 77: Hyperphenylalaninemia: Phenylalanine Hydroxylase Deficiency; The Online Metabolic and Molecular Bases of Inherited Disease; Aug. 31, 2018; 97 pp.
Tang et al.; Ingestion of Whey Hydrolysate, Casein, or Soy Protein Isolate: Effects On Mixed Muscle Protein Synthesis At Rest and Following Resistance Exercise in Young Men; J Appl Physiol 107: 987-992, 2009.
Keohane et al.; Influence of Protein Composition and Hydrolysis Method On Intestinal Absorption of Protein in Man; Gut; 1985; 26; 907-913.
MacLeod et al.; Breakfast With Glycomacropeptide Compared With Amino Acids Suppresses Plasma Ghrelin Levels in Individuals With Phenylketonuria; Mol Genet Metab. Aug. 2010; 100(4): 303-308.
MacLeod et al.; Nutritional Management of Phenylketonuria; Annales Nestle [Engl] 2010;68:58-69.
Metges et al.; Kinetics of L-[1-13C] Leucine When Ingested With Free Amino Acids, Unlabeled or Intrinsically Labeled Casein; Am J Physiol Endocrinol Metab 278: E1000-E1009, 2000.
Badem et al.; Production of Caseins and Their Usages; International Journal of Food Science and Nutrition ISSN: 2455-4898, Impact Factor: RJIF 5.14; www.foodsciencejournal.com; vol. 2; Issue 1; Jan. 2017; p. No. 04-09.
Pennings et al.; Whey Protein Stimulates Postprandial Muscle Protein Accretion More Effectively Than Do Casein and Casein Hydrolysate in Older Men 1-3; Am J Clin Nutr 2011;93:997-1005.
Didycz et al.; Dynamics of Hyperphenylalaninemia and Intellectual Outcome in Teenagers With Phenylketonuria; Acta ABP Biochimica Polonica; vol. 64, No. 3/2017 527-531.
Cleary et al.; Fluctuations in Phenylalanine Concentrations in Phenylketonuria: A Review of Possible Relationships With Outcomes; Molecular Genetics and Metabolism 110 (2013) 418-423.
Didycz et al.; Blood Phenylalanine Instability Strongly Correlates With Anxiety in Phenylketonuria; Molecular Genetics and Metabolism Reports 14 (2018) 80-82.
Romani et al.; The Impact of Phenylalanine Levels On Cognitive Outcomes in Adults With Phenylketonuria: Effects Across Tasks and Developmental Stages; Neuropsychology © 2017 The Author(s) 2017, vol. 31, No. 3, 242-254.
Solverson et al.; Glycomacropeptide, a Low-Phenylalanine Protein Isolated From Cheese Whey, Supports Growth and Attenuates Metabolic Stress in the Murine Model of Phenylketonuria; Am J Physiol Endocrinol Metab 302: E885-E895, 2012.
Hofman et al.; A Systematic Review of Cognitive Functioning in Early Treated Adults With Phenylketonuria; Hofman et al. Orphanet Journal of Rare Diseases (2018) 13:150.
Van Calcar et al.; Improved Nutritional Management of Phenylketonuria By Using a Diet Containing Glycomacropeptide Compared With Amino Acids 1-4; Am J Clin Nutr 2009;89:1068-77. Printed in USA. c. 2009 American Society for Nutrition.
APR Applied Pharma Research S.A.; International Application No. PCT/IB2019/056960 filed Aug. 17, 2019; International Search Report and Written Opinion; ISA/EP; Jan. 9, 2020; 12 pp.
Amidon, G. L., et al., "A theoretical basis for a biopharmaceutic drug classification: the correlation of in vitro drug product dissolution and in vivo bioavailability," Pharm Res 12(3):413-420, Springer Science+Business Media, Germany (Mar. 1995).
Anonymous, "Afenil Micro 3H," accessed online at URL:[http://www.piamfarmaceutici.com/Internet/medifood/Prodotti.aspx?P=100&C=12] on Dec. 9, 2016, 1 page (Jan. 2014). (Machine-Generated Translation of the Abstract).

Anonymous, "Afenil Micro 3H," accessed online at URL:[https://www.piamfarmaceutici.com/wp-content/uploads/2018/06/Afenil-micro-3H.pdf] on Dec. 13, 2019, 1 page (Dec. 2019).
Baracos, V. E., "Animal models of amino acid metabolism: a focus on the intestine," J Nutr 134(6 Suppl):1656S-1659S, Oxford University Press, United Kingdom (Jun. 2004).
Brosnan, J. T., and Brosnan, M. E., "Branched-chain amino acids: enzyme and substrate regulation," J Nutr 136(1 Suppl):207S-11S, Oxford University Press, United Kingdom (Jan. 2006).
Cole, J. T., "Metabolism of BCAAs" in Branched Chain Amino Acids in Clinical Nutrition, vol. 1, pp. 13-24, Rajendram, R., et al., eds., Humana Press, United States (Oct. 2015).
Cynober, L. A., "Plasma amino acid levels with a note on membrane transport: characteristics, regulation, and metabolic significance," Nutrition 18(9):761-766, Elsevier, Netherlands (Sep. 2002).
Giovannini, M., et al., "Randomized controlled trial of a protein substitute with prolonged release on the protein status of children with phenylketonuria," Journal of the American College of Nutrition 33(2):103-110, Taylor & Francis Group, LLC., United States (Mar. 2014).
International Search Report and Written Opinion for International Application No. PCT/IB2016/055773, European Patent Office, Netherlands, dated Dec. 21, 2016, 15 pages.
MacDonald, A., "The Dietary Management Of Phenylketonuria," Thesis, Department of Reproductive and Child Health School of Medicine, 289 pages, The University of Birmingham, Alabama (Aug. 1999).
Ney, D. M., et al., "Advances in the nutritional and pharmacological management of phenylketonuria," Current Opinion in Clinical Nutrition & Metabolic Care 17(1):61-68, Lippincott Williams and Wilkins Ltd., United States (Jan. 2014).
Ney, O. M., "Does the PKU diet contribute to impaired renal function?," Journal of Inherited Metabolic Disease 36(5):903-904, Springer, Netherlands (Sep. 2013).
Pena, M. J., et al., "Amino Acids, Glucose Metabolism and Clinical Relevance for Phenylketonuria Management," Annals of Nutritional Disorders & Therapy 2(3):1026, Austin Publishing Group, United States (2015).
Public Summary Document—Nov. 2015 PBAC Meeting, "Amino Acid Formula Without Phenylalanine, 110g modified release tablet × 4, bottle, PKU Easy Microtabs®, Orpharma Ply Ltd.," The Pharmaceutical Benefits Scheme, 6 pages, Australian Government Department of Health, Australia (Nov. 2015).
Rajendram, R., et al., eds., "Branched Chain Amino Acids in Clinical Nutrition," vol. 1, 270 pages, Humana Press, United States (Oct. 2015).
Van Spronsen, F. J., et al., "Large neutral amino acids in the treatment of PKU: from theory to practice," Journal of Inherited Metabolic Disease 33(6):671-676, Springer, Netherlands (Oct. 2010).
Van Vliet, D., et al., "Single amino acid supplementation in aminoacidopathies: a systematic review," Orphanet Journal of Rare Diseases 9:7, 14 pages, BioMed Central Ltd., United Kingdom (Jan. 2014).
Waisbren, S. E., et al., "Phenylalanine blood levels and clinical outcomes in phenylketonuria: a systematic literature review and meta-analysis," Mol Genet Metab 92(1-2):63-70, Elsevier, Netherlands (Sep.-Oct. 2007).
Whang, K. Y., and Easter, R. A., "Blood urea nitrogen as an index of feed efficiency and lean growth potential in growing-finishing swine," Asian-Australasian Journal of Animal Sciences 13(6):811-816, Asian-Australasian Journal of Animal Sciences, South Korea (2000).

* cited by examiner

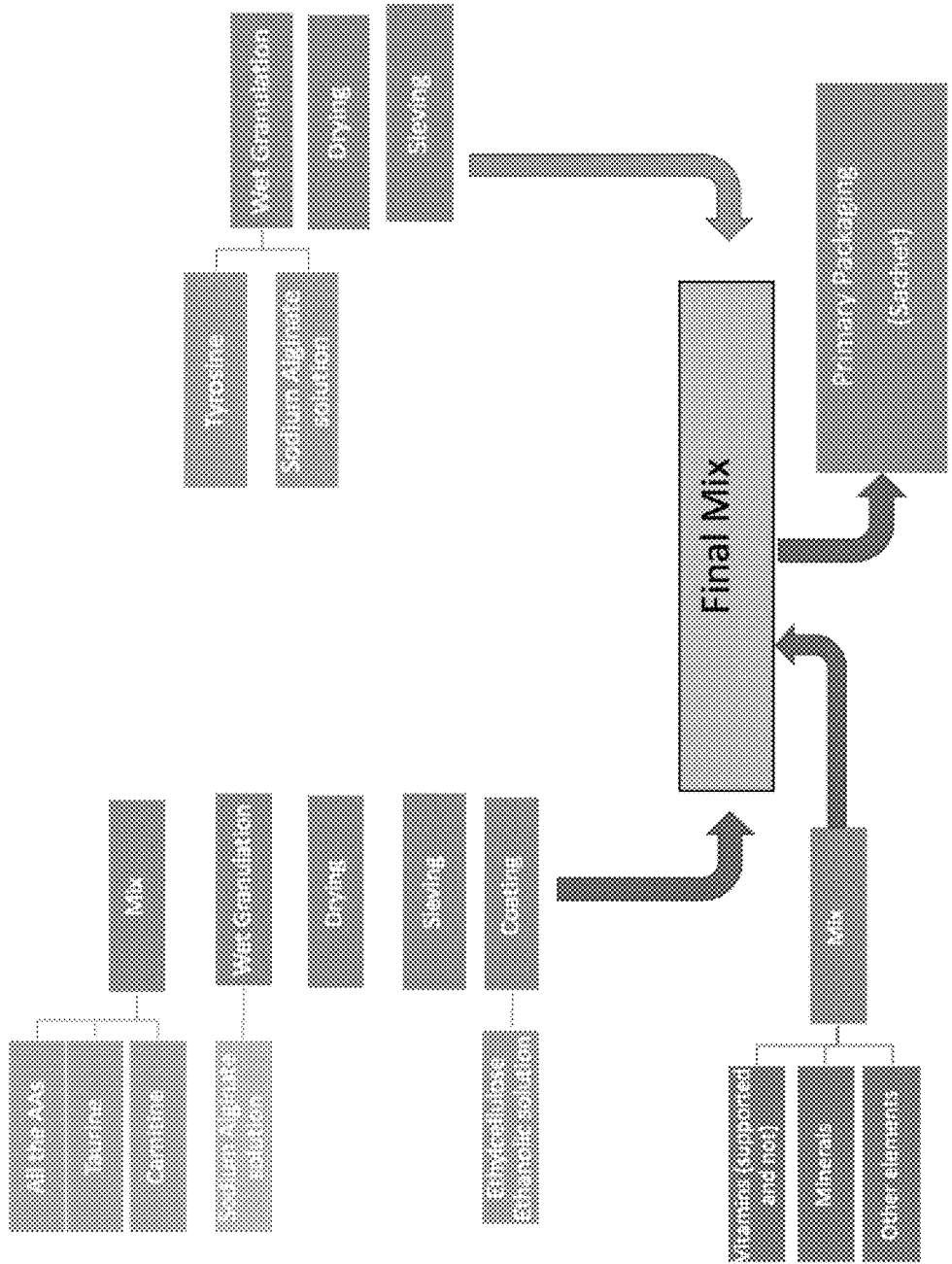
Figure 1: Manufacturing Flow Chart for Test Product.

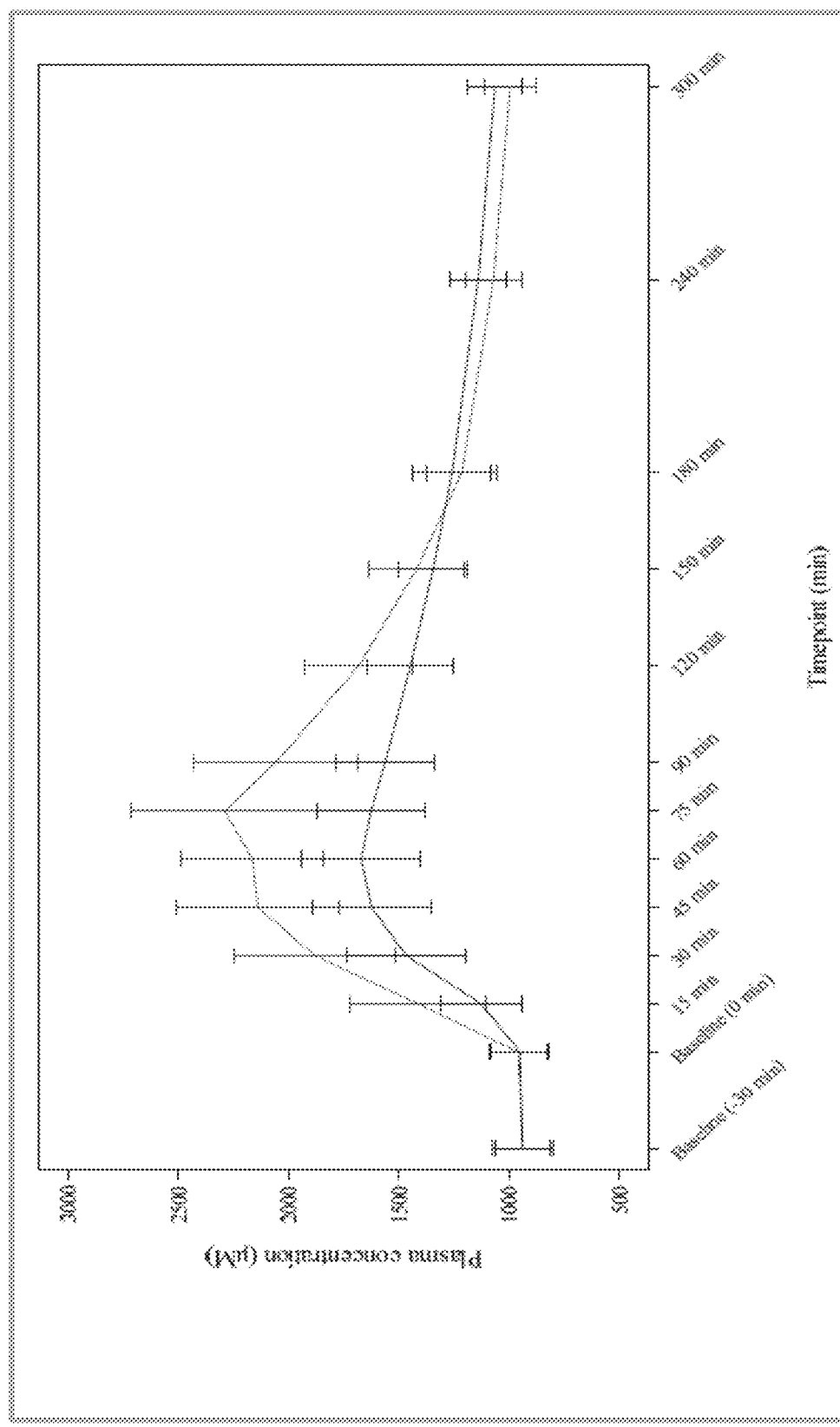
Figure 2: mean plasma concentration-time curve for essential AAs during 5 hours (300 min)

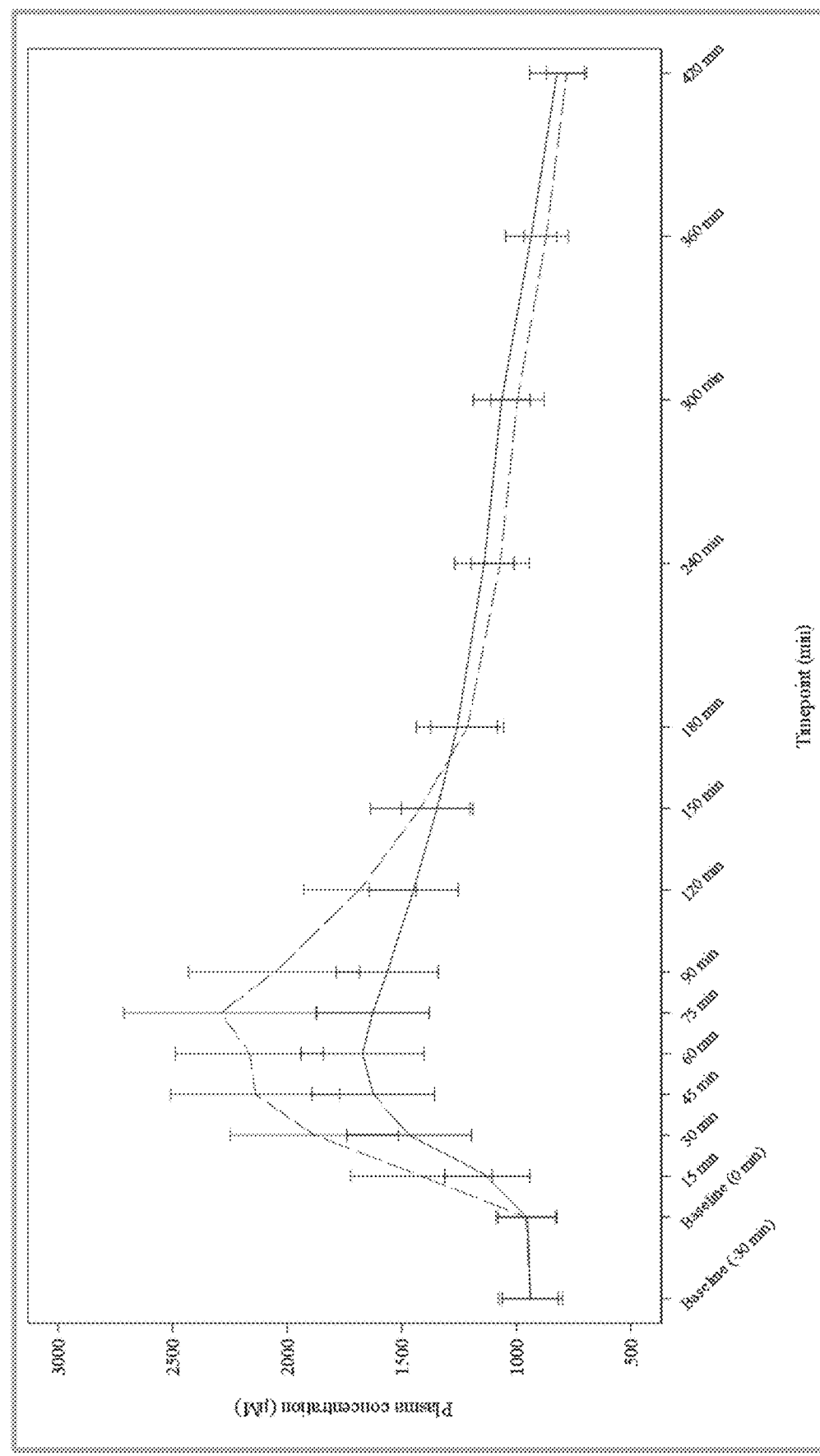
Figure 3: mean plasma concentration-time curve for essential AAs during 7 hours (420 min)

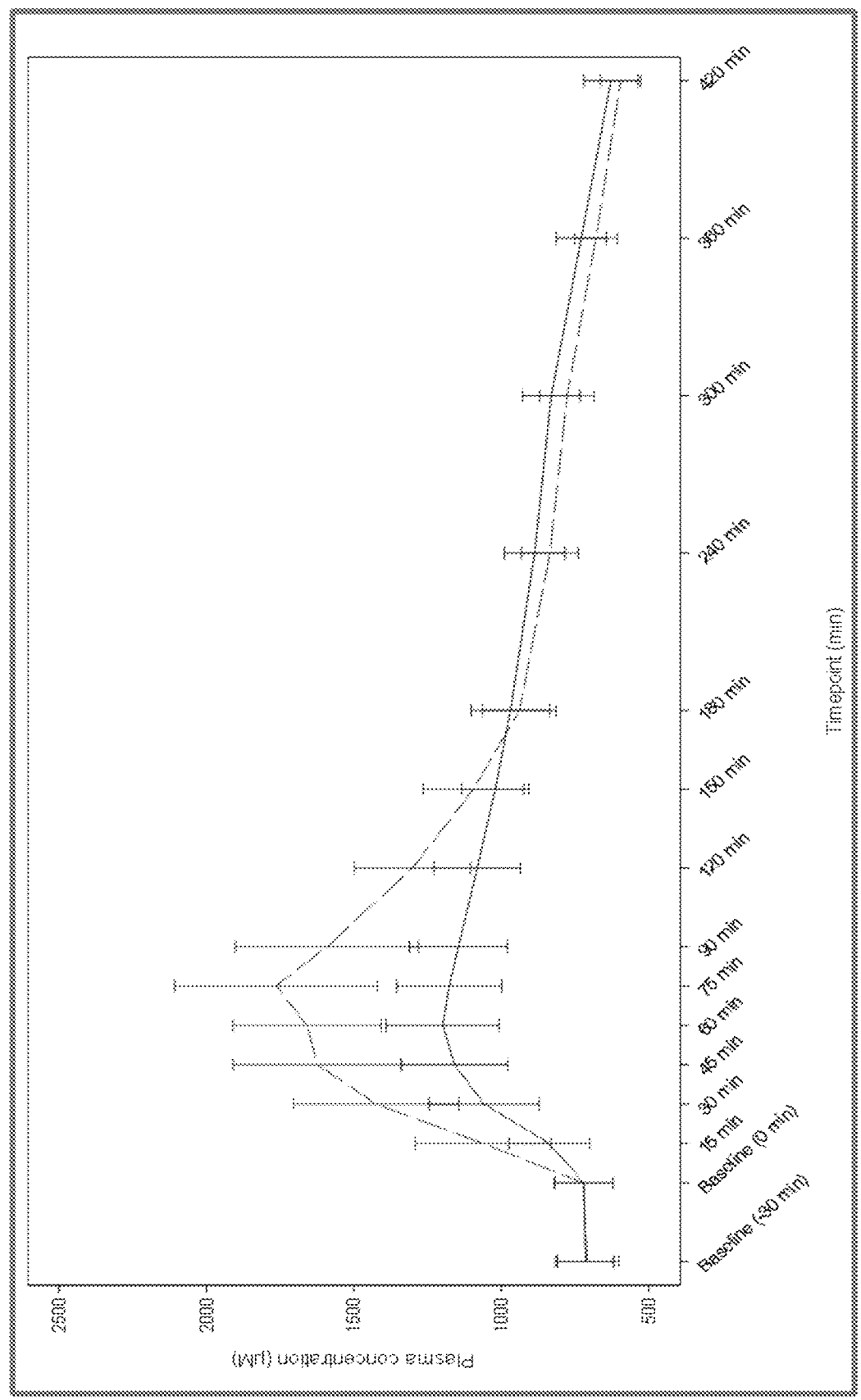
Figure 4: mean plasma concentration-time curve for large neutral AAs during 7 hours (420 min)

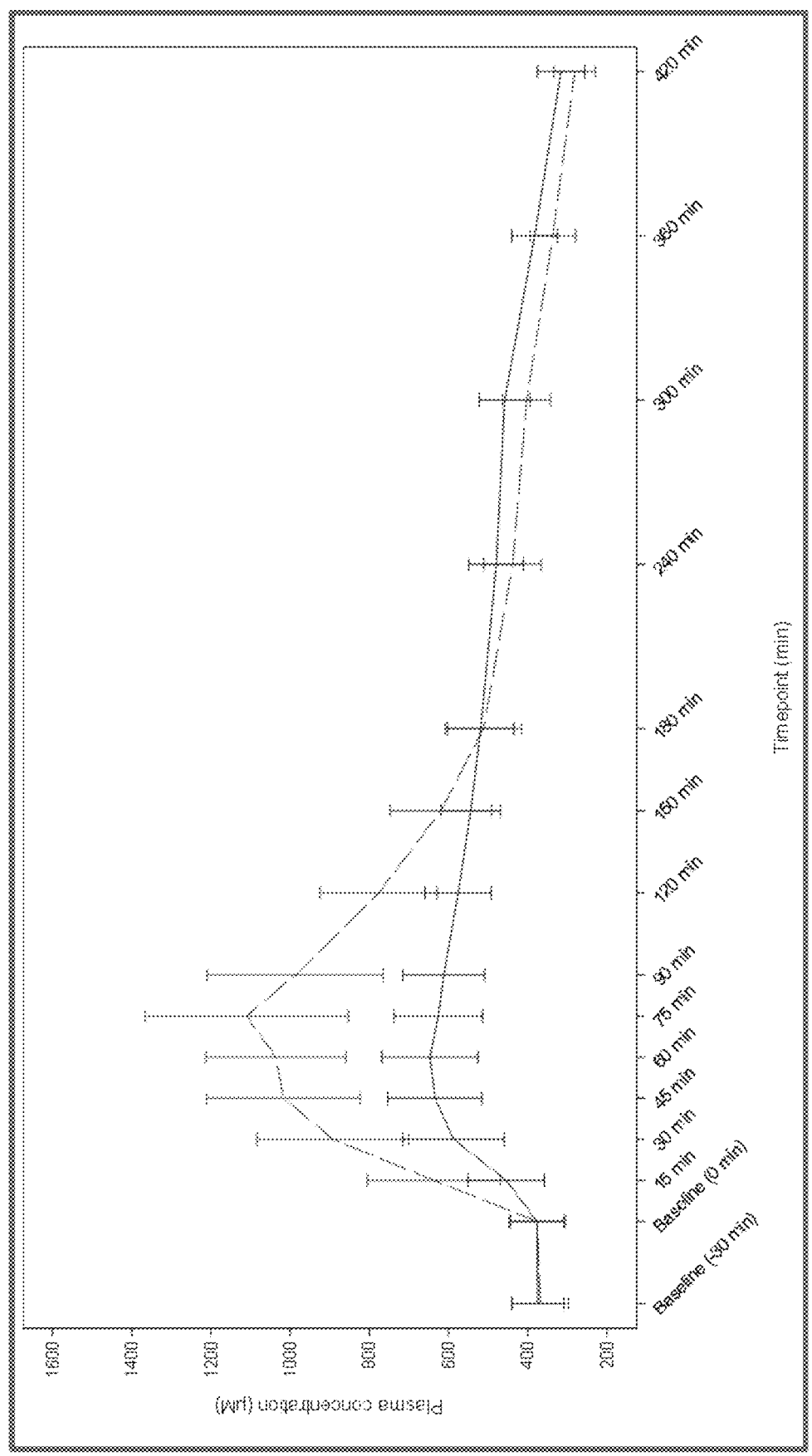
Figure 5: mean plasma concentration-time curve for branched chain AAs during 7 hours (420 min)

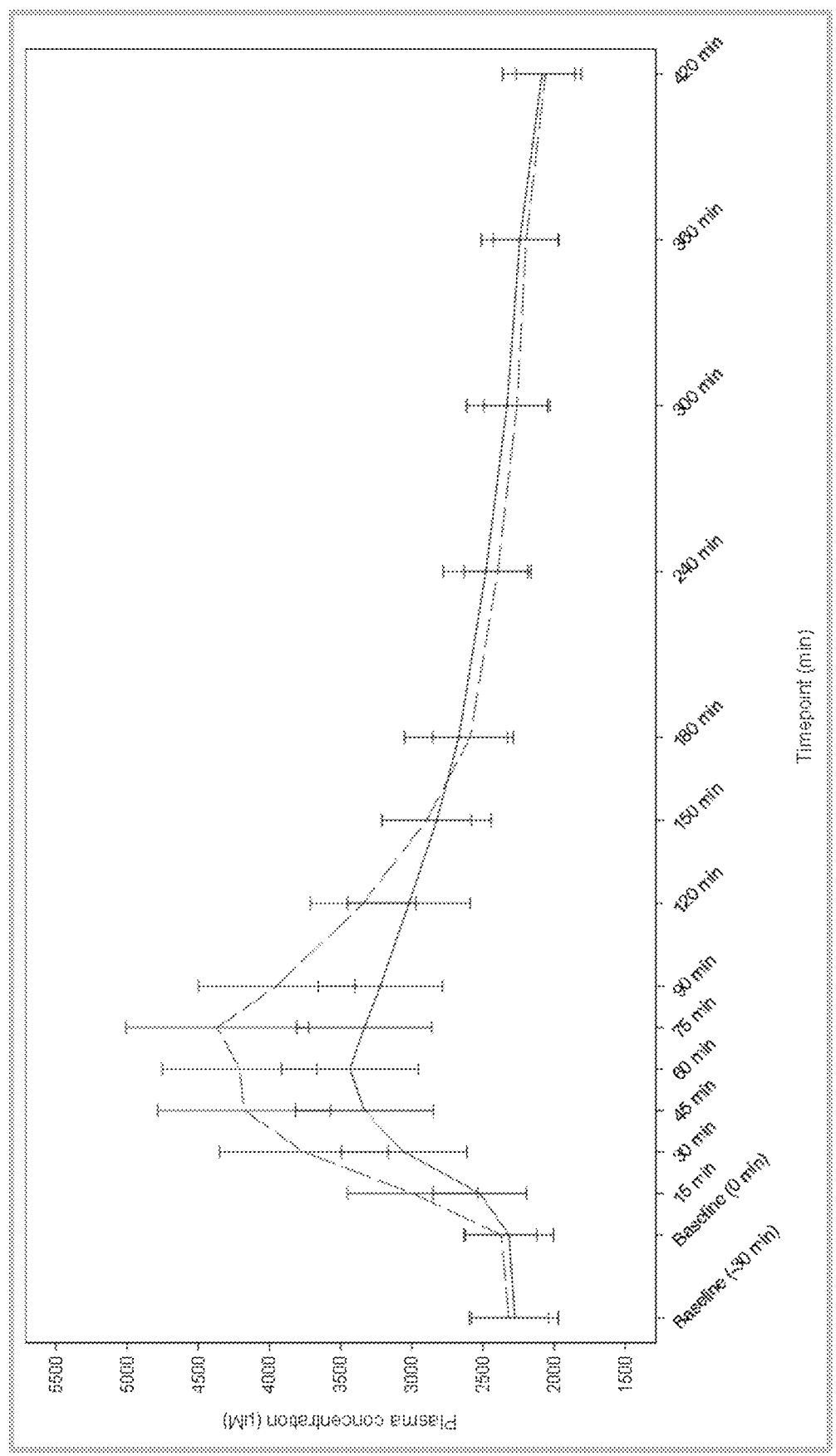
Figure 6: mean plasma concentration-time curve for total AAs during 7 hours (420 min)

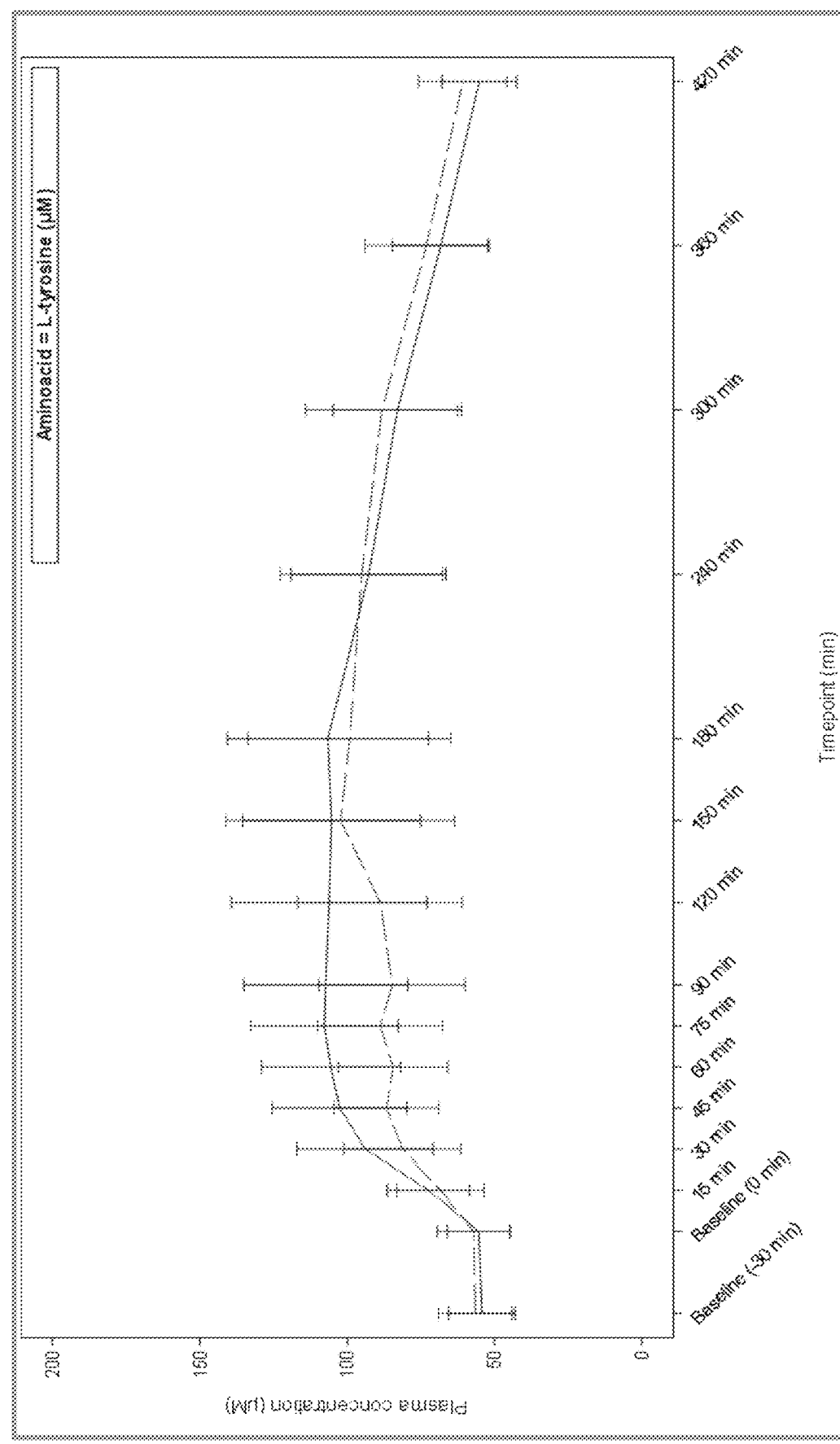
Figure 7: mean plasma concentration-time curve for tyrosine during 7 hours (420 min)

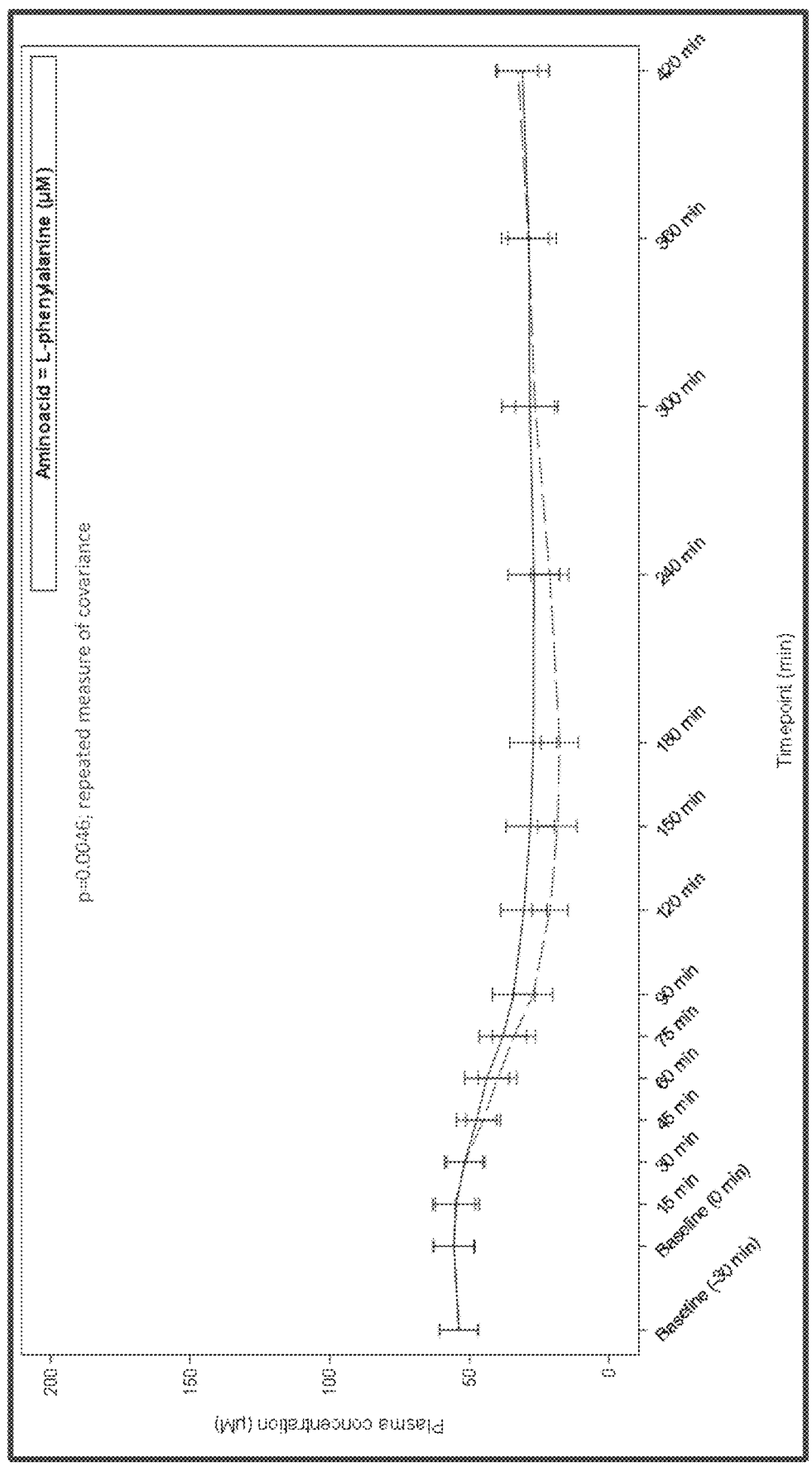
Figure 8: mean plasma concentration-time curve for phenylalanine during 7 hours (420 min)

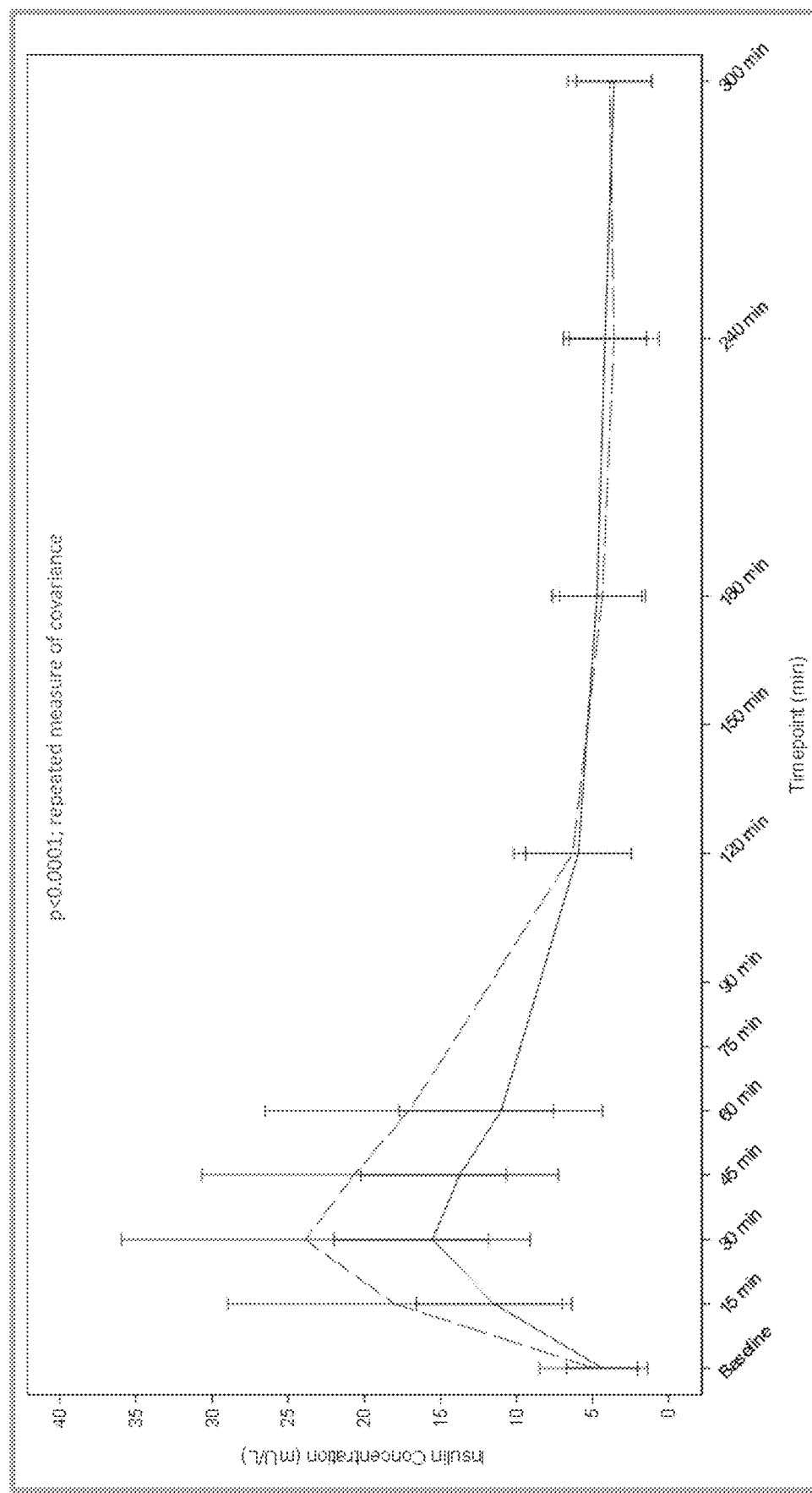
Figure 9: the mean plasma concentration-time curve for insulin during 5 hours (300 min)

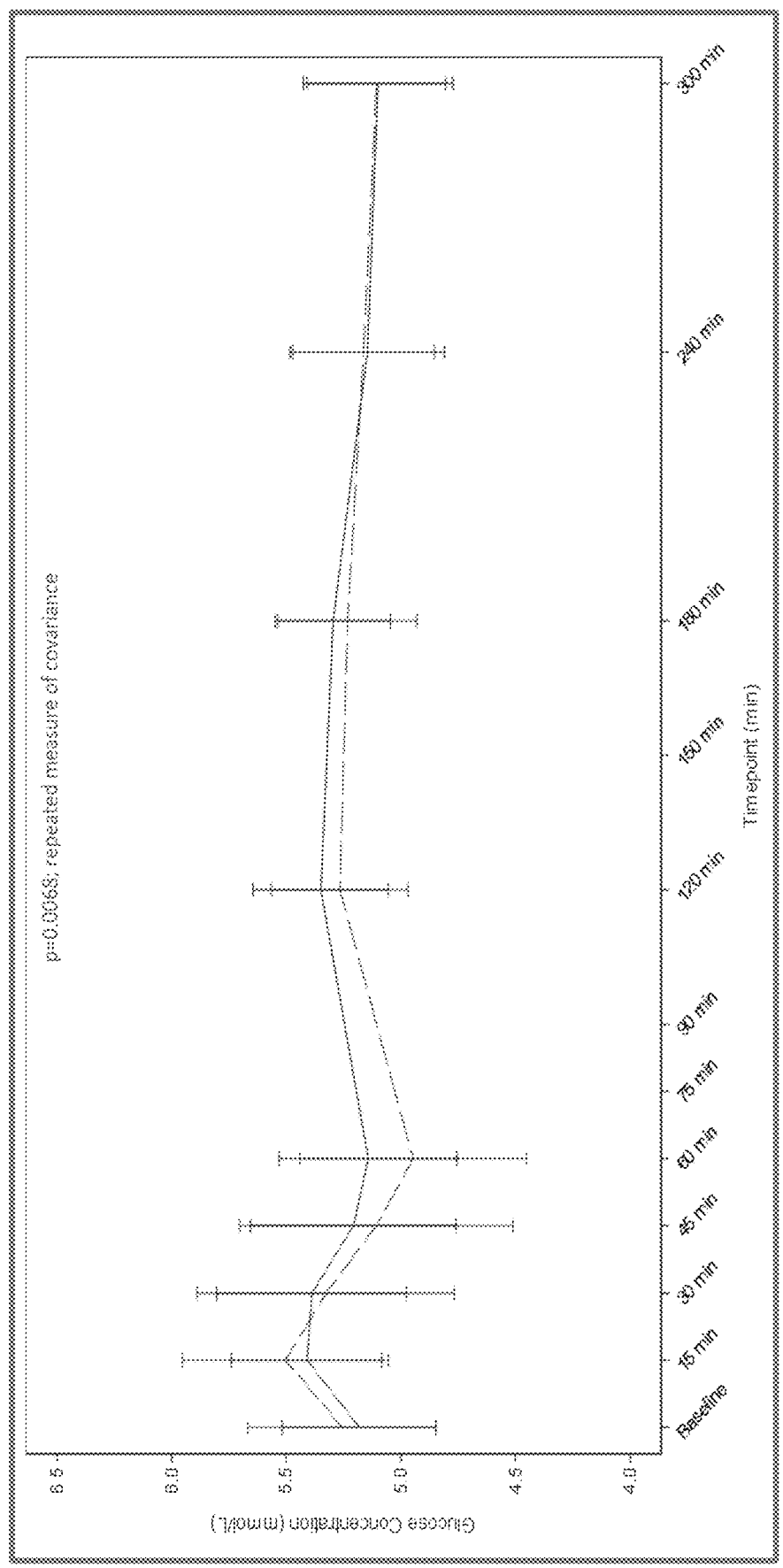
Figure 10: mean plasma concentration-time curve for glucose during 5 hours (300 min)

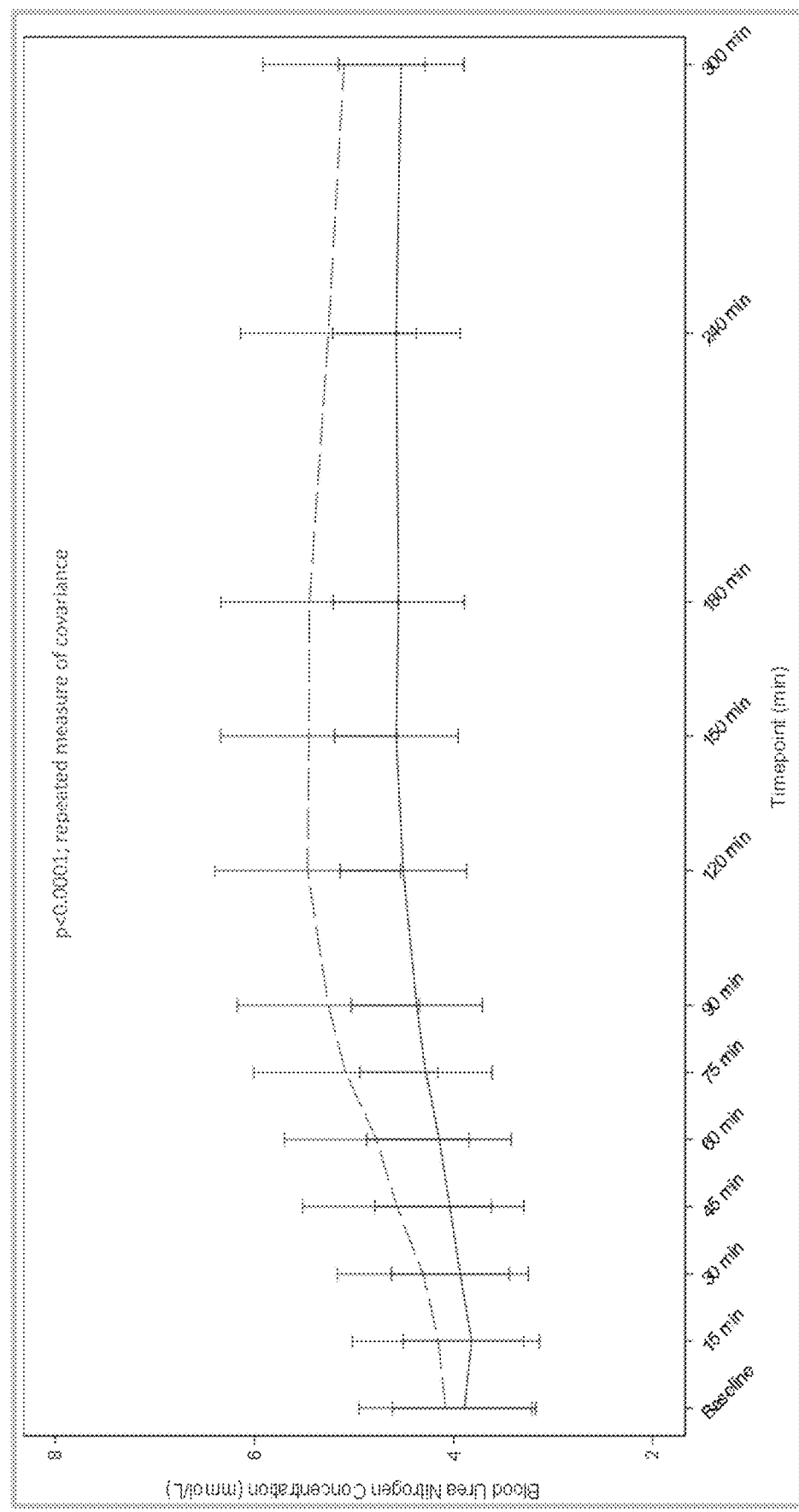
Figure 11: mean concentration-time curve for BUN in plasma during 5 hours (300 min)

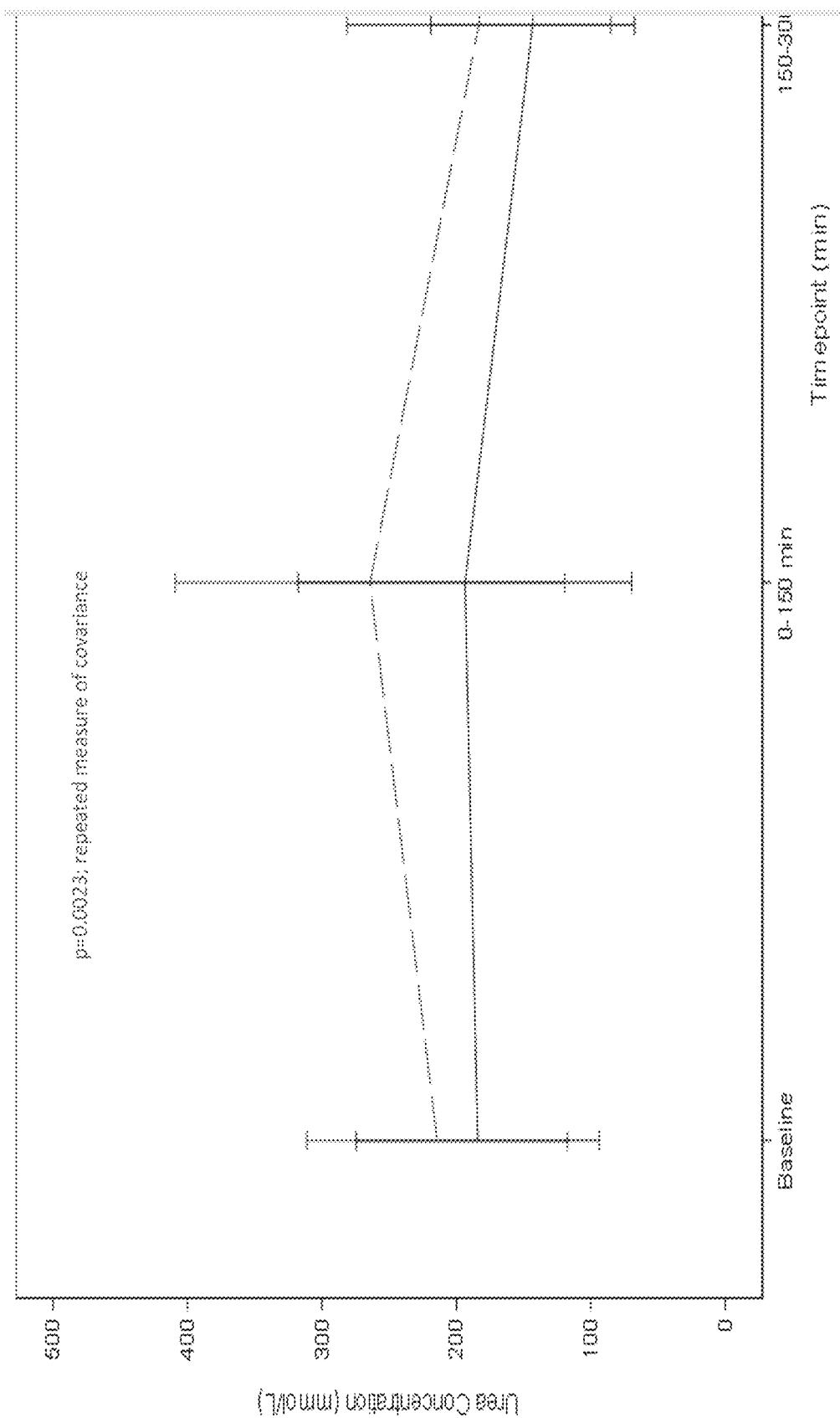
Figure 12: mean concentration-time curve for urea in urine, during 5 hours (300 min)

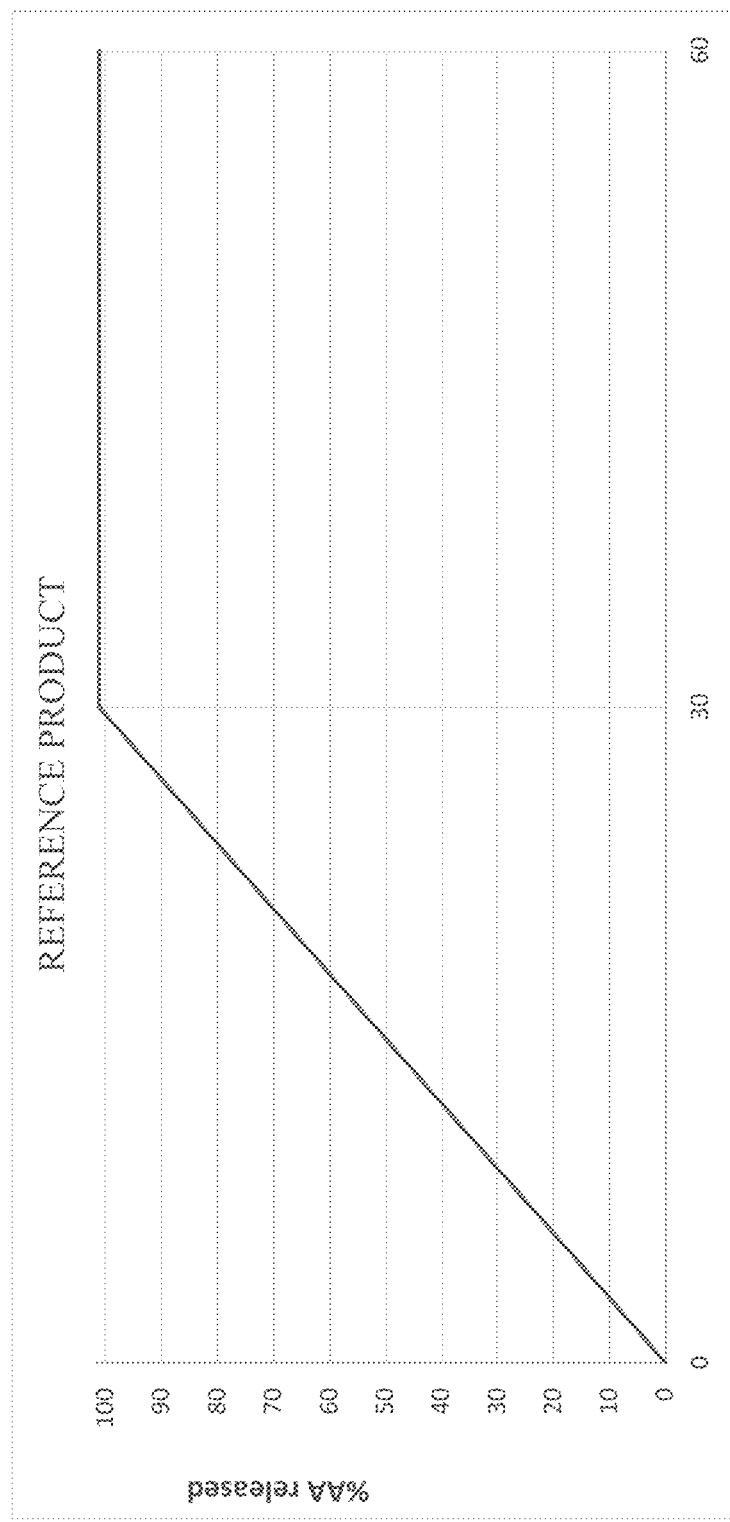
Figure 13: Ponderal dissolution test for total AAs being released over time (from 0 to 60 min) from the Reference Product

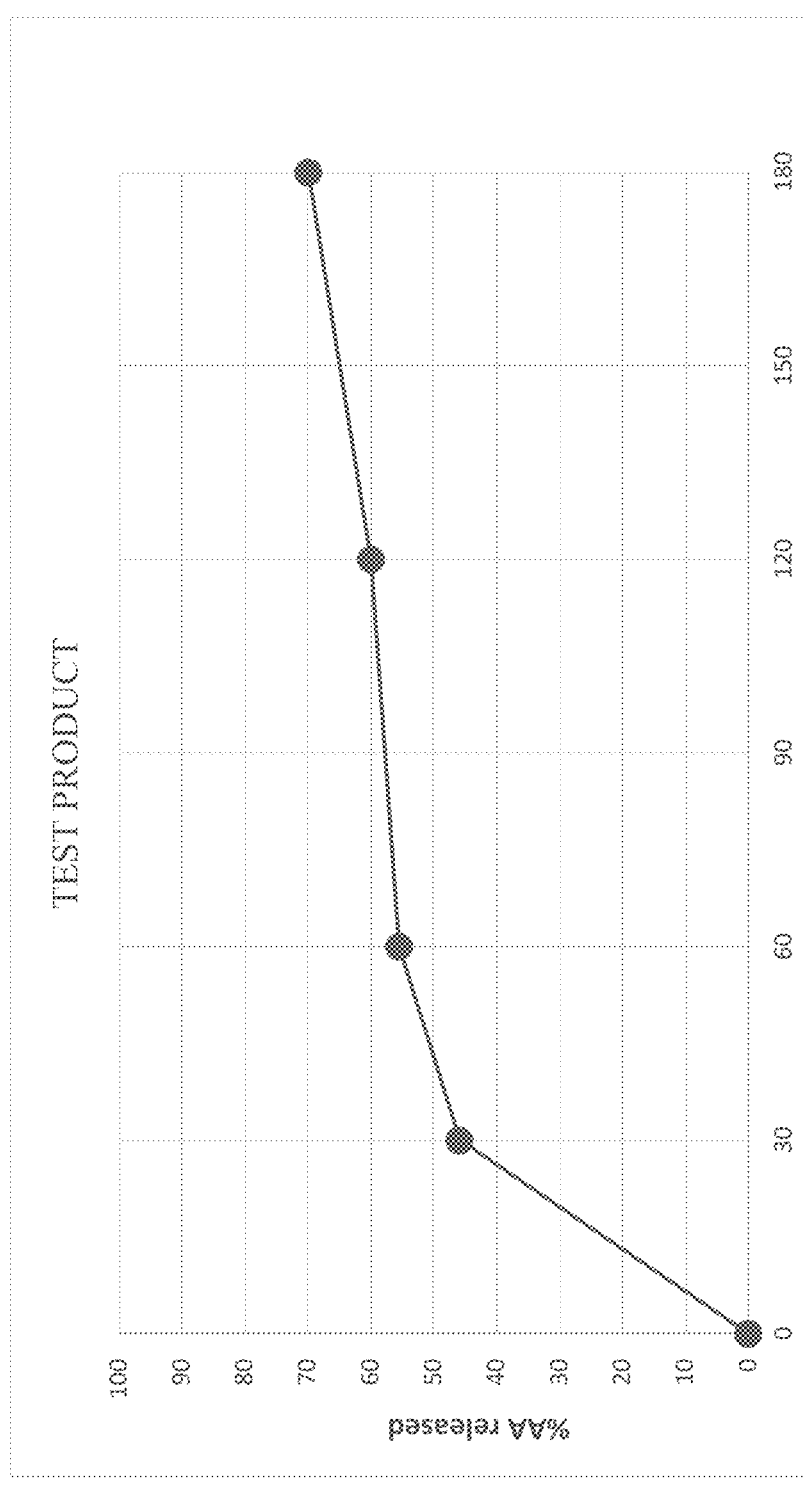
Figure 14: Ponderal dissolution test for total AAs being released over time (from 0 to 180 min) from the Test Product

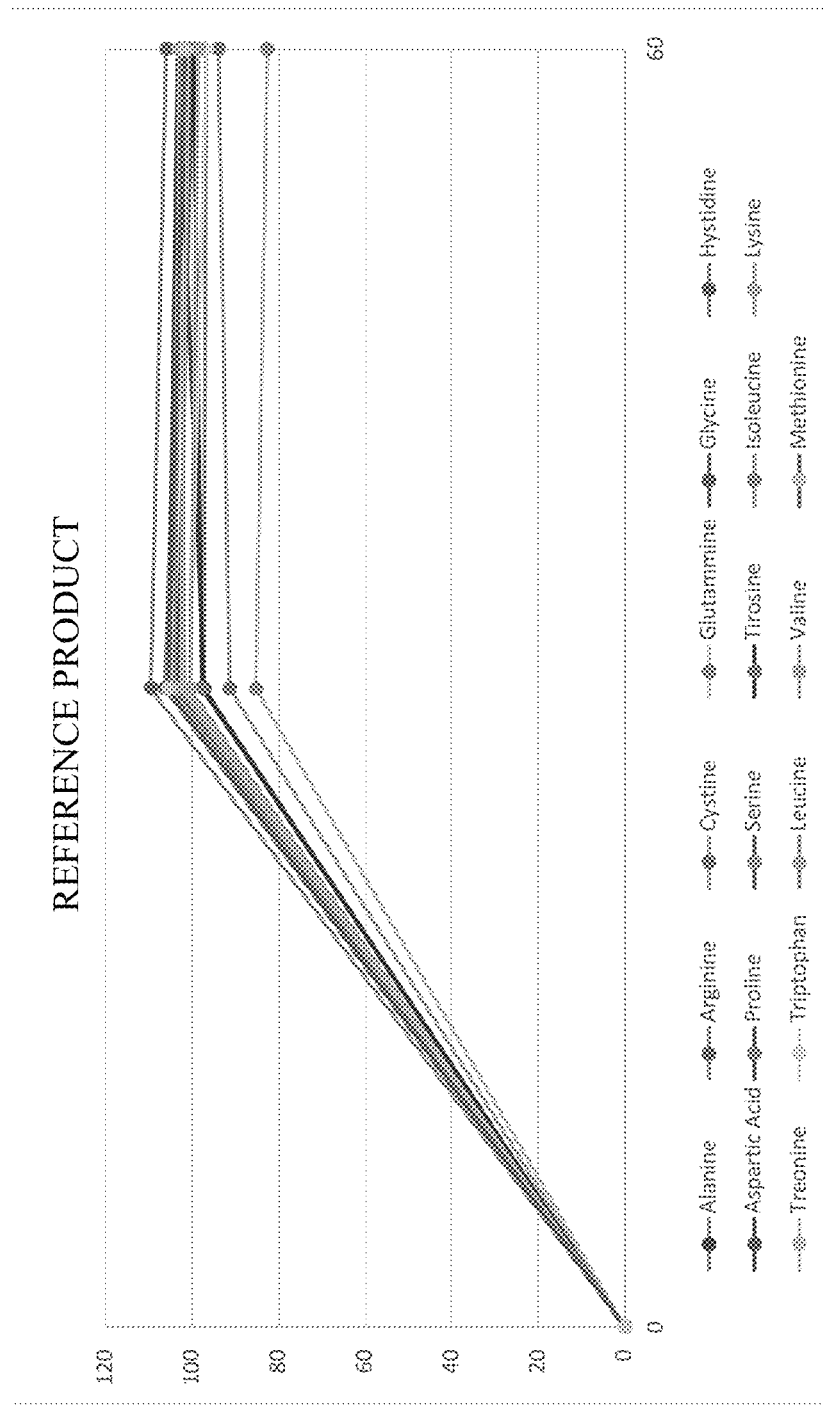
Figure 15: Dissolution test for individual AAs being released over time (from 0 to 60 min) from the Reference Product

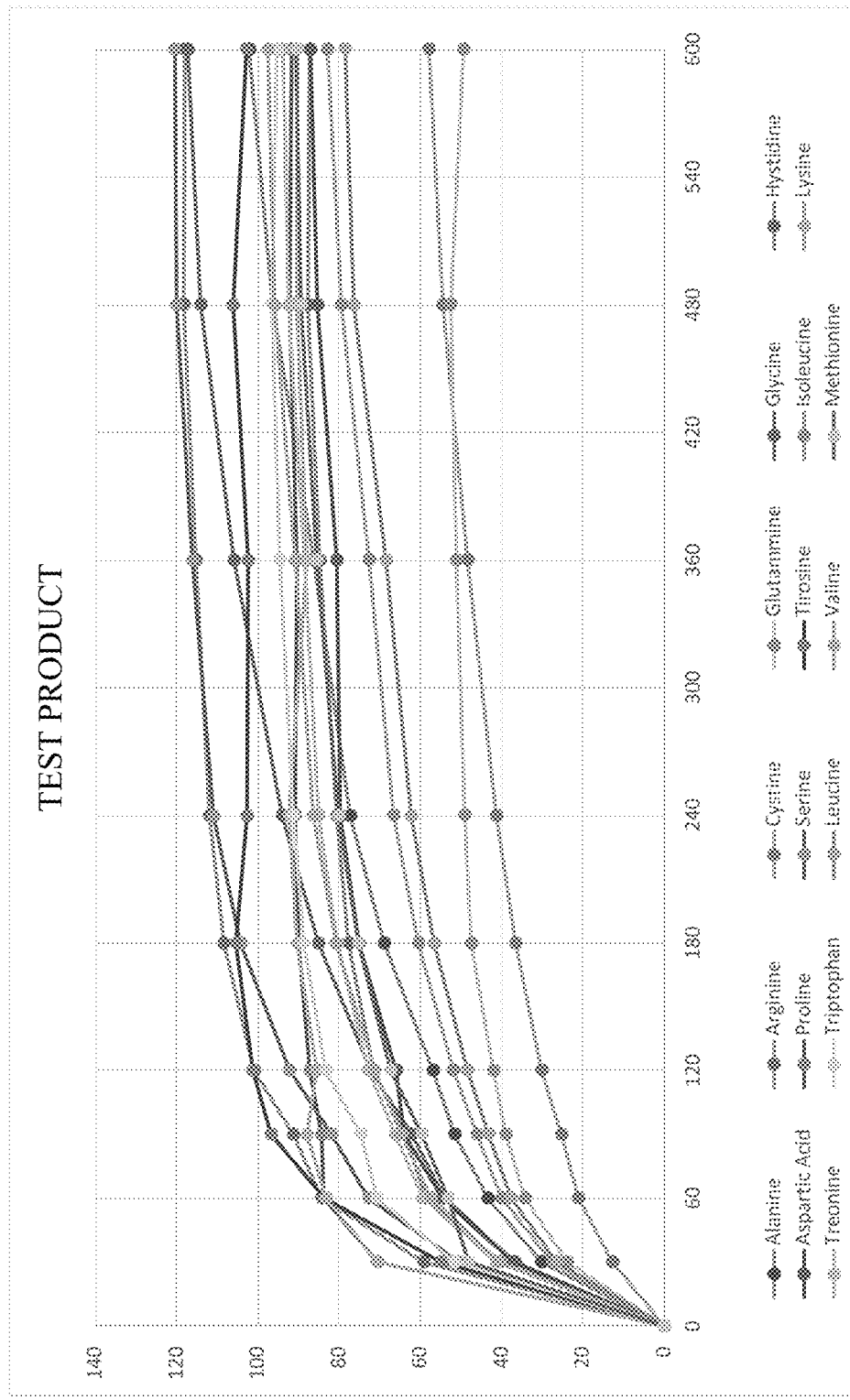
Figure 16. Dissolution test for individual AAs being released over time (from 0 to 600 min) from the Test Product

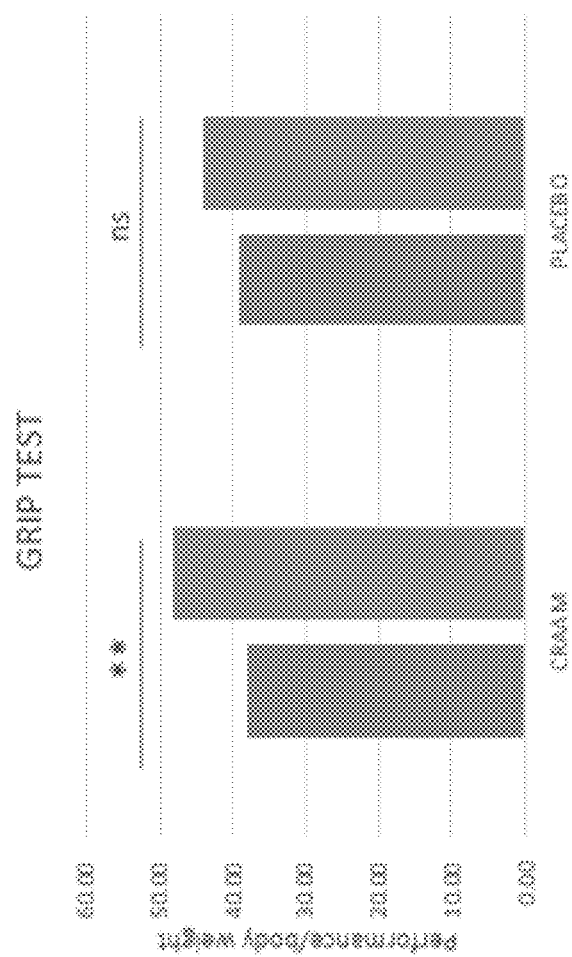
Figure 17. Strength of animals fed test and placebo amino acid formulations; basal strength is reported in the left bar; post-treatment strength is reported in right bar.

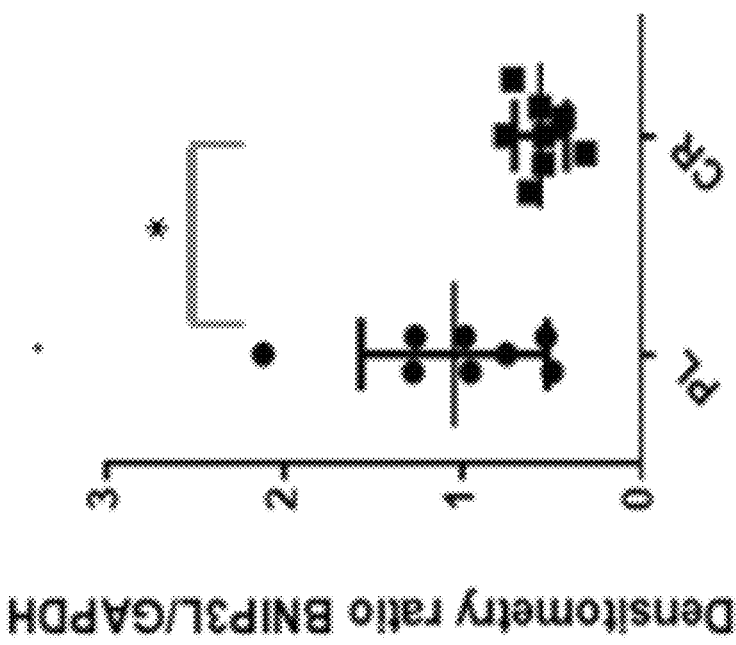
Figure 18. BNIP3L/NIX expression in the femoral biceps measured by Western Blot (PL = Placebo; CR = CRAAM / Test Formulation)

METHODS OF NORMALIZING AMINO ACID METABOLISM

FIELD OF THE INVENTION

The present invention relates to methods of normalizing impaired amino acid metabolism in subjects on a restricted protein diet supplemented by amino acids, including methods of treating medical conditions resulting from such impaired metabolism, using modified release formulations of amino acids that mimic the pharmacokinetic absorption of amino acids coming from intact natural proteins.

BACKGROUND

Several diseases are characterized by inborn errors of amino acid metabolism caused by deficient activities of enzymes necessary to process one or more amino acids. Phenylketonuria (PKU) is a prototypical example of such a disease, caused by deficient activity of the enzyme phenylalanine hydroxylase, which is needed to convert the essential amino acid phenylalanine to tyrosine. In individuals with PKU, phenylalanine is poorly or nil metabolized to tyrosine with a consequent increase of circulating levels of phenylalanine and its metabolites that produce toxic effects, especially in the central nervous system, if no suitable nutritional management is started.

As phenylalanine is an essential amino acid (i.e. it cannot be synthetized by the body but needs to be taken from diet), the goal of nutritional management of individuals with PKU is to maintain adequate plasma phenylalanine concentrations to support optimal growth, normal brain development, and mental functioning while providing a nutritionally complete diet and preventing neurological and psychological changes. Thus, individuals with PKU require lifelong adherence to a low-phenylalanine diet that is restricted in natural foods, in order to limit the intake of natural protein and, at the same time, to provide adequate amounts of phenylalanine, in addition to the intake of phenylalanine-free amino acid mixtures to meet their protein needs.

An alternative to synthetic amino acid mixtures has been available from 2010 onwards: i.e. glycomacropeptide (GMP), a natural 64-amino acid glycophosphopeptide derived from casein in bovine milk, which is produced during the manufacture of cheese. It is an alternative to phenylalanine-free synthetic amino acid mixtures with a potentially more natural absorption profile. However, GMP contains a residual amount of phenylalanine that could alter phenylalanine control.

When the major supply of protein substituents is of synthetic origin (readily absorbable phenylalanine-free amino acid mixtures), potential differences in the intake of protein versus the intake of free amino acids deserve special attention. It is known that efficient utilization of amino acids for the synthesis of body proteins is influenced by many factors, including rate of protein digestion and absorption of amino acids into the bloodstream, presence of all essential amino acids at the same time, and adequate intake of energy and total dietary nitrogen to support the high metabolic cost of protein synthesis (MacLeod and Ney 2010). Nitrogen requirements are thought to increase when the majority of amino acids is provided by an elemental free amino acid-based diet in comparison with intact natural proteins, due to the rapid absorption of amino acids after a free amino acid-based diet (Metges et al. 2000; Dangin et al. 2001; Gropper and Acosta 1991). This rapid absorption of amino acids into the bloodstream can impose a higher dietary acid load, particularly when higher doses are administered.

In healthy volunteers, dietary intake of free amino acids induced rapid absorption of amino acids into the bloodstream ($t_{max}$ of ~20-30 min), with high peak concentrations ($C_{max}$) (Gropper and Acosta 1991). This profile of absorption of amino acids was different from that commonly observed after the intake of natural proteins. As demonstrated by Gropper and Acosta (1991), plasma levels of total and essential amino acids were higher and peaked faster but decreased more quickly after oral intake of L-amino acid mixtures than after intake of a source of whole protein. Plasma amino acid concentrations after intake of whole protein peaked at 150 min whereas plasma amino acid concentrations after intake of free amino acid mixtures peaked at 30 min.

Dangin et al. (2001) evaluated the effects that a different amount/speed of absorption of amino acids by the gut into the bloodstream can exert on whole body protein synthesis, breakdown, and oxidation, and consequently on the control of protein deposition. In this study, post-prandial whole body kinetics was evaluated by comparing the intake of a single meal of casein (typical example of a slow-release protein) versus the intake of a free amino acid mixture (mimicking the amino acid composition of casein but acting as a fast-ingested meal), and by comparing the intake of a single meal of rapidly digested whey proteins versus repeated meals of whey proteins (mimicking a slow digestion rate), in healthy volunteers. Whole body leucine balance, an index of protein deposition and of the efficiency of post-prandial protein utilization, was shown to differ under different circumstances. "Fast" meals induced a strong, rapid and transient increase of amino acid levels in the bloodstream, in comparison with slow meals. This was associated with an increased protein synthesis and oxidation and only a transient/slight inhibition of protein breakdown. By contrast, the plasma appearance of amino acids after slow meals was slower, lower, and prolonged with a different whole body response: protein synthesis was not stimulated, oxidation was moderately stimulated, but protein breakdown was markedly inhibited.

The impact of chronic ingestion of amino acids on the kidney is of potential concern. Mice fed an amino acid diet demonstrated significant 15-30% increases in renal mass and urine volume, and an acidic urine pH <5.5 compared with mice fed a GMP diet (Solverson et al. 2012). In addition, the slower ingestion and absorption of GMP compared to amino acid mixtures promotes satiety and may modulate control of postprandial blood glucose levels (MacLeod et al. 2011; Van Calcar et al. 2009).

With the development of free amino acid formulas and dietary therapy, severe mental retardation due to PKU has abated. However, there are still substantial unmet medical needs for individuals with PKU of all age groups and genders, including those PKU patients having good control of phenylalanine levels obtained through a low-protein diet combined with the supplementation of free amino acid formulas or the use of existing available drugs.

Current unmet medical needs are mainly related to lifelong ingestion of synthetic, fast-absorbed free amino acid formulas. These clinical manifestations are mainly observed in classic PKU patients. Due to low phenylalanine tolerance, these patients have a diet composed mainly of free amino acid formulas which represent up to 80-85% of the total daily protein intake for their entire life.

New options are needed to provide an alternative to current synthetic free amino acid mixtures and improve the dietary management of individuals who consume large quantities of free amino acids.

SUMMARY OF INVENTION

The inventors have unexpectedly discovered several advantages from mimicking the digestion of proteins in patients on restricted protein diets supplemented by amino acids, including an improved nitrogen balance, reduced muscle catabolism, improved glucose and insulin control, and reduced fluctuations in amino acid concentrations, with consequent metabolic, and musculoskeletal benefits.

Thus, in a first principal embodiment, the invention provides a method of treating or preventing elevated amino acid concentrations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a second principal embodiment the invention provides a method of treating or preventing elevated phenylalanine concentrations or fluctuations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids. This second principal embodiment is particularly applicable to PKU patients, wherein the supplemental oral amino acids exclude phenylalanine.

In a third principal embodiment the invention provides a method of treating or preventing muscle proteolysis manifesting as weight or muscle loss or elevated BUN or urea concentrations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a fourth principal embodiment the invention provides a method of treating or preventing elevated BUN or urea concentrations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a fifth principal embodiment the invention provides a method of stabilizing glucose levels and reducing insulin levels in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a sixth principal embodiment the invention provides a method of stabilizing tyrosine absorption in a subject on a restricted protein diet supplemented by oral amino acids comprising administering to said subject a therapeutically effective amount of the formulation of an amino acid formulation comprising granulated particles of tyrosine and alginic acid or a pharmaceutically acceptable salt thereof, uncoated by a modified release coating. This sixth principal embodiment is particularly applicable to PKU patients, wherein the supplemental oral amino acids exclude phenylalanine.

In a seventh principal embodiment the invention provides a method of normalizing one or more metabolic markers selected from plasma insulin, plasma glucose, blood urea nitrogen, urine urea nitrogen, and plasma phenylalanine in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the invention and together with the description serve to explain the principles of the invention.

FIG. 1 is a manufacturing flow chart for the Test Product used in Example 1.

FIG. 2 plots the mean plasma concentration-time curve for essential amino acids during 5 hours (300 min) from Test and Reference Products as described in Example 1. The dashed line denotes Reference Product results; the solid line denotes Test Product results.

FIG. 3 plots the mean plasma concentration-time curve for essential amino acids during 7 hours (420 min) from Test and Reference Products as described in Example 1. The dashed line denotes Reference Product results; the solid line denotes Test Product results.

FIG. 4 plots the mean plasma concentration-time curve for large neutral amino acids during 7 hours (420 min) for from Test and Reference Products as described in Example 1. The dashed line denotes Reference Product results; the solid line denotes Test Product results.

FIG. 5 plots the mean plasma concentration-time curve for branched chain amino acids during 7 hours (420 min) from Test and Reference Products as described in Example 1. The dashed line denotes Reference Product results; the solid line denotes Test Product results.

FIG. 6 plots the mean plasma concentration-time curve for total amino acids during 7 hours (420 min) from Test and Reference Products as described in Example 1. The dashed line denotes Reference Product results; the solid line denotes Test Product results.

FIG. 7 plots the mean plasma concentration-time curve for tyrosine during 7 hours (420 min) from Test and Reference Products as described in Example 1. The dashed line denotes Reference Product results; the solid line denotes Test Product results.

FIG. 8 plots the mean plasma concentration-time curve for phenylalanine during 7 hours (420 min) from Test and Reference Products as described in Example 1. The dashed line denotes Reference Product results; the solid line denotes Test Product results.

FIG. 9 plots the mean plasma concentration-time curve for insulin during 5 hours (300 min) from Test and Reference Products as described in Example 1. The dashed line denotes Reference Product results; the solid line denotes Test Product results.

FIG. 10 plots the mean plasma concentration-time curve for glucose during 5 hours (300 min) from Test and Reference Products as described in Example 1. The dashed line denotes Reference Product results; the solid line denotes Test Product results.

FIG. 11 plots the mean concentration-time curve for BUN in plasma during 5 hours (300 min) from Test and Reference Products as described in Example 1. The dashed line denotes Reference Product results; the solid line denotes Test Product results.

FIG. 12 plots the mean concentration-time curve for urea in urine, during 5 hours (300 min) from Test and Reference Products as described in Example 1. The dashed line denotes Reference Product results; the solid line denotes Test Product results.

FIG. 13 is a graphical plot of the ponderal dissolution test results for the sum of amino acids released over time from the Reference Product described in Example 1, measured according to the method described in Example 3.

FIG. 14 is a graphical plot of the ponderal dissolution test results for the sum of amino acids released over time from the Test Product described in Example 1, measured according to the method described in Example 3.

FIG. 15 is a graphical plot of the dissolution test results for the individual amino acids released over time from the Reference Product described in Example 1, measured according to the method described in Example 3.

FIG. 16 is a graphical plot of dissolution test results for the individual amino acids released over time from the Test Product described in Example 1, measured according to the method described in Example 3.

FIG. 17 is a bar graph depicting changes over time in grip strength in animals fed a modified release formulation of the present invention and animals fed a placebo, as described in Example 4. Baseline results are reported in the left bar on each graph; end of study results are reported on the right.

FIG. 18 is a graph depicting BNIP3L/NIX expression in the femoral biceps measured by Western Blot in the animal study reported in Example 4. PL results correspond to placebo; CR results correspond to the test formulation.

DETAILED DESCRIPTION

Definitions and Use of Terms

Wherever an analysis or test is required to understand a given property or characteristic recited herein, it will be understood that the analysis or test is performed in accordance with applicable guidances, draft guidances, regulations and monographs of the United States Food and Drug Administration ("FDA") and United States Pharmacopoeia ("USP") applicable to drug products in the United States in force as of Aug. 30, 2018 unless otherwise specified.

As used in this specification and in the claims which follow, the singular forms "a," "an" and "the" include plural referents unless the context clearly dictates otherwise.

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality components, steps or conditions, it will be understood that the element can also be described as comprising any combination of such plurality, or "consisting of" or "consisting essentially of" the plurality or combination of components, steps or conditions.

When ranges are given by specifying the lower end of a range separately from the upper end of the range, or specifying particular numerical values, it will be understood that a range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

When used herein the term "about" will compensate for variability allowed for in the pharmaceutical industry and inherent in products in this industry, such as differences in product strength due to manufacturing variation and time-induced product degradation. The term allows for any variation which in the practice of good manufacturing practices would allow the product being evaluated to be considered therapeutically equivalent or bioequivalent in humans to the recited strength of a claimed product as described in FDA's March 2003 Guidance for Industry on Bioavailability and Bioequivalence Studies for Orally Administered Drug Products—General Considerations.

When percentages are given herein, it will be understood that the percentages are weight percent, and that proportions are based on weight, unless otherwise stated to the contrary.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

The term "amino acid" refers to any naturally occurring amino acid capable of participating in the synthesis of peptides and proteins. For ease of drafting, the amino acid will frequently be written without its stereo-configuration, although it will be understood that the amino acid should be present as its naturally occurring stereoisomer. In the formulations of the present invention, amino acids can be present as the free base, as the hydrochloride salt, or as another suitable salt.

"Bioequivalence" means the absence of a significant difference in the rate and extent to which the active ingredient or active moiety in pharmaceutical equivalents or pharmaceutical alternatives become available at the site of drug action when administered at the same molar dose under similar conditions in an appropriately designed study. Area under the curve (AUC) bioequivalence means that the mean AUC of a test product is from 80% to 125% of the mean AUC of a reference product in a suitably designed crossover trial, over a time period of 300 minutes, 420 minutes, or extrapolated to infinity.

The term "formulation" refers to a finished or semi-finished combination of pharmaceutical or medical food or food ingredients, including both active ingredients and inactive excipients or additives. The term refers to in-process formulations, finished formulations, and formulations packaged as a final unit dose.

The term "modified release" refers to any pharmaceutical formulation in which the release rate is intentionally altered to achieve a desired therapeutic or pharmacokinetic response. The term thus includes extended release formulations, in which the release of the drug is extended over time, or a release rate that is independent of the pH of the surrounding environment. The term also includes delayed release formulations, where the release of active ingredient from the formulation (or a portion thereof) is delayed to occur after the initial ingestion. A delayed release formulation is typically designed so that release occurs predominantly once the formulation reaches the small intestine.

Discussion

The invention is described in terms of principal embodiments and subembodiments, and it will be understood that the principal embodiments can be combined to define other principal embodiments, that the subembodiments can be combined to define additional subembodiments, and that the subembodiments and combinations of subembodiments can be combined with all of the principal embodiments to define further embodiments of the present invention. The ability to combine embodiments and subembodiments is limited only by what is mathematically or physically impossible.

Thus, in a first principal embodiment, the invention provides a method of treating or preventing elevated amino acid concentrations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a second principal embodiment the invention provides a method of treating or preventing elevated phenylalanine concentrations or fluctuations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a third principal embodiment the invention provides a method of treating or preventing muscle proteolysis manifesting as weight or muscle loss or elevated BUN or urea concentrations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a fourth principal embodiment the invention provides a method of treating or preventing elevated BUN or urea concentrations in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a fifth principal embodiment the invention provides a method of stabilizing glucose levels and reducing insulin levels in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

In a sixth principal embodiment the invention provides a method of stabilizing tyrosine absorption in a subject on a restricted protein diet supplemented by oral amino acids comprising administering to said subject a therapeutically effective amount of the formulation of an amino acid formulation comprising granulated particles of tyrosine and alginic acid or a pharmaceutically acceptable salt thereof, uncoated by a modified release coating.

In a seventh principal embodiment the invention provides a method of normalizing one or more metabolic markers selected from plasma insulin, plasma glucose, blood urea nitrogen, urine urea nitrogen, and plasma phenylalanine in a subject on a restricted protein diet supplemented by oral amino acids comprising administering to said subject a therapeutically effective amount of a modified release amino acid formulation, thereby prolonging the release of said oral amino acids and mimicking the metabolism of natural proteins by said amino acids.

Discussion of Subembodiments

In various embodiments the elevated amino acid or phenylalanine concentrations manifest in an unhealthy condition or have the potential to manifest in an unhealthy condition and the administration of the modified release amino acids treat or prevent the unhealthy condition, particularly in patients suffering from unhealthy phenylalanine concentrations. Thus, in one subembodiment the elevated phenylalanine concentrations manifest as a condition selected from an intellectual disability, anxiety, depression, an executive functioning deficit, a cognitive deficit, a reduced intelligence quotient, seizures, delayed development, behavioral problems, a psychiatric disorder, unstable moods, inability to focus, tremors, information processing delays, memory deficits, body protein deficits, height deficits, bone loss, muscle weakness, gait disorders, decreased energy, or lethargy, and the modified release amino acids treat or prevent the condition. In another subembodiment the elevated amino acid concentrations manifest as a condition selected from weight or muscle loss or elevated BUN or urea concentrations and the modified release amino acids treat or prevent the condition. In still another subembodiment the elevated amino acid concentrations manifest as a condition selected from unstable glucose or elevated insulin levels and the modified release amino acids treat or prevent the condition.

The methods and formulations are particularly useful for supplementing individuals with inborn errors of metabolism with special dietary needs for amino acids. Thus, in some embodiments the subject suffers a metabolic disorder selected from the group consisting of phenylketonuria, tyrosinemia, leucinosis, methylmalonic acidemia, homocystinuria, hyperglycinemia, isovaleric acidemia, propionic acidemia, and glutamic acidemia, in a subject in need thereof. In other embodiments the subject has chronic kidney disease, liver disease, diabetes, cardiovascular disease, sarcopenia, cachexia, or low plasma albumin (>3.5 g/L$^{-1}$), or the subject is recovering from neurosurgery, or the subject is in need of increased muscle mass for sporting activities, or the subject is involved in another activity where amino acid supplementation is desired.

In still further subembodiments the subject has PKU selected from one of three severities:

classic PKU, defined as a phenylalanine concentration of greater than 1200 micromole/L (20 mg/dL), and the modified release amino acid formulation lacks phenylalanine.

mild PKU, defined as a phenylalanine concentration of from 600 to 1200 micromole/L (from 10 to 20 mg/dL), and the modified release amino acid formulation lacks phenylalanine.

mild hyperphenylalaninemia, defined as a phenylalanine concentration of from 300 to 600 micromole/L (from 5 to 10 mg/dL), and the modified release amino acid formulation lacks phenylalanine.

Daily regimens of amino acids balanced in relative amounts to meet the physiological needs of said subject typically comprise from 0.8 to 1.35 g/kg/day in the formulations of the present invention. Subjects can be divided into 3 weight & energy categories as follows: 55-65.4 kg body weight subjects preferably receive 24 g amino acids (dose) corresponding to 20.0 g protein equivalents thrice daily; 65.5-75.4 kg body weight subjects preferably receive 28 g amino acids (dose) corresponding to 23.3 g protein equivalents thrice daily; 75.5-85 kg body weight subjects preferably receive 32 g amino acids (dose) corresponding to 26.6 g protein equivalents thrice daily.

In one subembodiment the amino acid formulation comprises as amino acids 5, 10, or all of the following amino acids: 0.47 to 0.97 weight parts of L-alanine, 0.66 to 1.26 weight parts of L-arginine, 1.04 to 1.84 weight parts of L-aspartic acid, 0.28 to 0.68 weight parts of L-cystine, 4.1 to 5.6 weight parts of L-glutamine, 0.9 to 1.5 weight parts of L-glycine, 0.5 to 0.85 weight parts of L-histidine, 1.0 to 1.65 weight parts of L-isoleucine, 2.25 to 3.25 weight parts of L-leucine, 1.45 to 2.0 weight parts of L-lysine, 0.23 to 0.43 weight parts of L-methionine, 0.0000 weight parts of L-phenylalanine, 1.2 to 1.8 weight parts of L-proline, 0.6 to 1.1 weight parts of L-serine, 0.9 to 1.6 weight parts of L-threonine, 0.35 to 0.65 weight parts of L-tryptophan, 2.0 to 3.0 weight parts of L-tyrosine, and 0.9 to 1.6 weight parts of L-valine.

In another subembodiment the amino acid formulation comprises 0.7200 weight parts of L-alanine, 0.9600 weight parts of L-arginine, 1.4400 weight parts of L-aspartic acid, 0.4800 weight parts of L-cystine, 4.8000 weight parts of L-glutamine, 1.2000 weight parts of L-glycine, 0.6710 weight parts of L-histidine, 1.3200 weight parts of L-isoleucine, 2.7600 weight parts of L-leucine, 1.6800 weight parts of L-lysine, 0.3334 weight parts of L-methionine, 1.4400 weight parts of L-proline, 0.8134 weight parts of L-serine, 1.2000 weight parts of L-threonine, 0.4800 weight parts of L-tryptophan, 2.400 weight parts of L-tyrosine, and 1.2000 weight parts of L-valine.

In one subembodiment the method and formulation produces: (a) an amino acid pharmacokinetic profile substantially as depicted in FIG. 6; and/or (b) an amino acid $C_{max}$ of less than 4400, 4300, 4200, 4100, 4000, 3900, 3800, 3700, or 3600 µM. The pharmacokinetics are preferably observed from a single administration of 24.0 g of amino acids to a 60 kg subject.

In still another subembodiment the formulation comprising as amino acids 0.7200 g of L-alanine, 0.9600 g of L-arginine, 1.4400 g of L-aspartic acid, 0.4800 g of L-cystine, 4.8000 g of L-glutamine, 1.2000 g of L-glycine, 0.6710 g of L-histidine, 1.3200 g of L-isoleucine, 2.7600 g of L-leucine, 1.6800 g of L-lysine, 0.3334 g of L-methionine, 0.0000 g of L-phenylalanine, 1.4400 g of L-proline, 0.8134 g of L-serine, 1.2000 g of L-threonine, 0.4800 g of L-tryptophan, 2.400 g of L-tyrosine, and 1.2000 g of L-valine, produces: (a) an amino acid pharmacokinetic profile substantially as depicted in FIG. 6; and/or (b) an amino acid $C_{max}$ of less than 4400, 4300, 4200, 4100, 4000, 3900, 3800, 3700, or 3600 µM. The pharmacokinetics are preferably observed from a single administration of 24.0 g of amino acids to a 60 kg subject.

In another subembodiment (a) said modified release amino acids produce a maximum concentration of total amino acids in blood following oral administration of at least 20% less than the maximum concentration of total amino acids in blood following oral administration of an equal quali-quantitative dose of immediate release amino acids; and or (b) said modified release amino acids produce an area under the curve (AUC) of total amino acids in blood following oral administration bioequivalent to the AUC produced by oral administration of an equal quali-quantitative dose of immediate release amino acids. The pharmacokinetics are preferably observed from a single administration of 24.0 g of amino acids to a 60 kg subject.

In another subembodiment the amino acid formulation comprises as essential amino acids 4, 7, or all of the following amino acids: 0.66 to 1.26 weight parts of L-arginine, 0.5 to 0.85 weight parts of L-histidine, 1.0 to 1.65 weight parts of L-isoleucine, 2.25 to 3.25 weight parts of L-leucine, 1.45 to 2.0 weight parts of L-lysine, 0.23 to 0.43 weight parts of L-methionine, 0.9 to 1.6 weight parts of L-threonine, 0.35 to 0.65 weight parts of L-tryptophan, 2.0 to 3.0 weight parts of L-tyrosine, and 0.9 to 1.6 weight parts of L-valine.

In still another subembodiment the amino acid formulation comprises as essential amino acids 0.6710 weight parts of L-histidine, 1.3200 weight parts of L-isoleucine, 2.7600 weight parts of L-leucine, 1.6800 weight parts of L-lysine, 0.3334 weight parts of L-methionine, 1.2000 weight parts of L-threonine, 0.4800 weight parts of L-tryptophan, 1.2000 weight parts of L-valine, 0.9600 weight parts of L-arginine, and 2.400 weight parts of L-tyrosine.

In another subembodiment the formulation produces: (a) an essential amino acid pharmacokinetic profile substantially as depicted in FIG. 2; and/or (b) an essential amino acid $C_{max}$ of less than 2300, 2200, 2100, 2000, 1900, or 1800 µM. The pharmacokinetics are preferably observed from a single administration of 24.0 g of amino acids including 13.00 g of essential amino acids to a 60 kg subject.

In another subembodiment a formulation comprising as essential amino acids 0.6710 g of L-histidine, 1.3200 g of L-isoleucine, 2.7600 g of L-leucine, 1.6800 g of L-lysine, 0.3334 g of L-methionine, 1.2000 g of L-threonine, 0.4800 g of L-tryptophan, 1.2000 g of L-valine, 0.9600 g of L-arginine, and 2.400 g of L-tyrosine produces: (a) an essential amino acid pharmacokinetic profile substantially as depicted in FIG. 2; and/or (b) an essential amino acid $C_{max}$ of less than 2300, 2200, 2100, 2000, 1900, or 1800 µM. The pharmacokinetics are preferably observed from a single administration of 24.0 g of amino acids including 13.00 g of essential amino acids to a 60 kg subject.

In another subembodiment (a) said modified release amino acids produce a maximum concentration of essential amino acids in blood following oral administration of at least 20% less than the maximum concentration of essential amino acids in blood following oral administration of an equal quali-quantitative dose of immediate release essential amino acids; and or (b) said modified release amino acids produce an area under the curve (AUC) of essential amino acids in blood following oral administration bioequivalent to the AUC produced by oral administration of an equal quali-quantitative dose of immediate release essential amino acids. The pharmacokinetics are preferably observed from a single administration of 24.0 g of amino acids including 13.00 g of essential amino acids to a 60 kg subject.

In another subembodiment the formulation comprises as large neutral amino acids 3, 5, or all of the following amino acids: 0.5 to 0.85 weight parts of L-histidine, 1.0 to 1.65 weight parts of L-isoleucine, 2.25 to 3.25 weight parts of L-leucine, 0.23 to 0.43 weight parts of L-methionine, 0.9 to 1.6 weight parts of L-threonine, 0.35 to 0.65 weight parts of L-tryptophan, 2.0 to 3.0 weight parts of L-tyrosine, and 0.9 to 1.6 weight parts of L-valine.

In still another subembodiment the formulation comprises as large neutral amino acids 0.6710 weight parts of L-histidine, 1.3200 weight parts of L-isoleucine, 2.7600 weight parts of L-leucine, 0.3334 weight parts of L-methionine, 1.200 weight parts of L-threonine, 0.4800 weight parts of L-tryptophan, 1.200 weight parts of L-valine, and 2.400 weight parts of L-tyrosine.

In another subembodiment the formulation produces: (a) a large neutral amino acid pharmacokinetic profile substantially as depicted in FIG. 4; and/or (b) a large neutral amino acid $C_{max}$ of less than 1700, 1600, 1500, 1400, or 1300 μM. The pharmacokinetics are preferably observed from a single administration of 24.0 g of amino acids including 10.36 g of large neutral amino acids to a 60 kg subject.

In another subembodiment the formulation comprising as large neutral amino acids 0.6710 g of L-histidine, 1.3200 g of L-isoleucine, 2.7600 g of L-leucine, 0.3334 g of L-methionine, 1.200 g of L-threonine, 0.4800 g of L-tryptophan, 1.200 g of L-valine, and 2.400 g of L-tyrosine produces: (a) a large neutral amino acid pharmacokinetic profile substantially as depicted in FIG. 4; and/or (b) a large neutral amino acid $C_{max}$ of less than 1700, 1600, 1500, 1400, or 1300 μM. The pharmacokinetics are preferably observed from a single administration of 24.0 g of amino acids including 10.36 g of large neutral amino acids to a 60 kg subject.

In another subembodiment (a) said modified release amino acids produce a maximum concentration of large neutral amino acids in blood following oral administration of at least 20% less than the maximum concentration of large neutral amino acids in blood following oral administration of an equal quali-quantitative dose of immediate release large neutral amino acids; and/or (b) said modified release amino acids produce an area under the curve (AUC) of large neutral amino acids in blood following oral administration bioequivalent to the AUC produced by oral administration of an equal quali-quantitative dose of large neutral immediate release amino acids. The pharmacokinetics are preferably observed from a single administration of 24.0 g of amino acids including 10.36 g of large neutral amino acids to a 60 kg subject.

In another subembodiment the amino acid formulation comprises as branched chain amino acids 1, 2 or all of the following amino acids: 1.0 to 1.65 weight parts of L-isoleucine, 2.25 to 3.25 weight parts of L-leucine, and 0.9 to 1.6 weight parts of L-valine. In still another subembodiment the amino acid formulation comprises as branched chain amino acids 1.200 weight parts of L-valine, 2.7600 weight parts of L-leucine, and 1.3200 weight parts of L-isoleucine.

In another subembodiment the formulation produces: (a) a branched chain amino acid pharmacokinetic profile substantially as depicted in FIG. 5; and/or (b) a branched chain amino acid $C_{max}$ of less than 1100, 1000, 900, 800, or 700 μM. The pharmacokinetics are preferably observed from a single administration of 24.0 g of amino acids including 5.28 g of branched chain amino acids to a 60 kg subject.

In another subembodiment the formulation comprising as branched chain amino acids 1.200 g of L-valine, 2.7600 g of L-leucine, and 1.3200 g of L-isoleucine produces: (a) a branched chain amino acid pharmacokinetic profile substantially as depicted in FIG. 5; and/or (b) a branched chain amino acid $C_{max}$ of less than 1100, 1000, 900, 800, or 700 μM. The pharmacokinetics are preferably observed from a single administration of 24.0 g of amino acids including 10.36 g of large neutral amino acids to a 60 kg subject.

In another subembodiment: (a) said modified release amino acids produce a maximum concentration of branched chain amino acids in blood following oral administration of at least 20% less than the maximum concentration of branched chain amino acids in blood following oral administration of an equal quali-quantitative dose of immediate release branched chain amino acids; and/or (b) said modified release amino acids produce an area under the curve (AUC) of branched chain amino acids in blood following oral administration bioequivalent to the AUC produced by oral administration of an equal quali-quantitative dose of branched chain immediate release amino acids. The pharmacokinetics are preferably observed from a single administration of 24.0 g of amino acids including 10.36 g of large neutral amino acids to a 60 kg subject.

In other subembodiments the formulation comprises one, all or any combination of amino acids selected from L-alanine, L-arginine, L-aspartic acid, L-cystine, L-glutamine, L-glycine, L-histidine, L-isoleucine, L-leucine, L-lysine, L-methionine, L-proline, L-serine, L-threonine, L-tryptophan, L-tyrosine, and L-valine.

In other subembodiments the formulation comprises one, all or any combination of essential amino acids selected from L-histidine, L-isoleucine, L-leucine, L-lysine, L-methionine, L-threonine, L-tryptophan, L-valine, L-arginine, and L-tyrosine.

In other subembodiments the formulation comprises one, all or any combination of large neutral amino acids selected from L-isoleucine, L-leucine, L-methionine, L-threonine, L-tryptophan, L-valine, L-tyrosine, and L-histidine In other subembodiments the formulation comprises one, all or any combination of branched chain amino acids selected from L-valine, L-leucine, and L-isoleucine.

Final Formulation

In one subembodiment the formulation comprises granulates of amino acids coated by one or more release modifying excipients, also referred to herein as "coating means for retarding the amino acid release rate," or "coating means for achieving the recited release rate." The granulates can be made by wet or dry granulation techniques, as discussed above, but they are preferably made by wet granulation. They are also preferably confined to a particular size range, such as 0.1-3 mm, 0.5-2.0 mm, 0.5-1.0 mm, 0.5-2.0 mm, or 1.0-2.0 mm. Each amino acid can be contained within its own granulate, but the modified release amino acids are preferably mixed within the granulates.

The modified release properties are preferably achieved with a suitable release modifying coating or coatings applied to the granulate, in an amount of from 1 wt % to 30 wt %, or from 5 wt % to 25 wt % based on the weight of the amino acids. Suitable release retarding excipients for the coating include ethylcellulose, glyceryl dibehenate, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, stearyl alcohol, acrylic acid copolymers, sodium alginate, carrageenan, alginic acid, pectin, sodium carboxymethyl cellulose, or a combination thereof.

One preferred composition comprises granulated particles having one of the foregoing size ranges and a coating of from 1 wt % to 15 wt %, from 2 wt % to 10 wt %, or from 5 wt % to 7.5 wt % ethylcellulose based on the weight of the amino acids. Another preferred composition comprises granulated particles having one of the foregoing size ranges and a first coating of ethylcellulose (as described above) and a second coating of from 5% to 15% or about 10 wt. % glyceryl dibehenate based on the weight of the amino acids.

In other subembodiments the formulation comprising 2 g of the modified release amino acids releases no more than 70% or 60% or 50% of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm.

In other subembodiments the modified release amino acids are present in particles comprising a binder selected from polyvinyl pyrrollidone, starch, methylcellulose, hydroxypropyl methylcellulose, carboxymethyl cellulose, sucrose solution, dextrose solution, guar gum, xanthan gum, acacia, tragacanth, locust bean gum and sodium alginate, or an alginic acid salt, preferably sodium alginate or another salt of alginic acid. In other subembodiments the modified release amino acids are present in particles comprising a modified release coating comprising ethylcellulose or a combination of ethylcellulose and diglyceryl dibehenate.

In other subembodiments the modified release amino acids are present in particles comprising: (a) a binder selected from sodium alginate or a salt of alginic acid; and (b) a modified release coating comprising ethylcellulose or a combination of ethylcellulose and diglyceryl dibehenate. In other subembodiments the formulation further comprises granulated particles of tyrosine uncoated by a modified release coating, having a binder selected from alginic acid and salts thereof.

The formulations of the present invention can also comprise other nutritional additives. Thus, in another subembodiment the formulation further comprises one or more additional ingredients selected from the group consisting of: (a) vitamins, minerals and carbohydrates; or (b) choline, inositol, vitamin A, vitamin D, vitamin E, vitamin K, vitamin C, thiamin, riboflavin, niacin, vitamin B6, folate, vitamin B12, biotin, pantothenic acid, potassium, calcium, magnesium, iron, zinc, copper, manganese, selenium, chromium, molybdenum, iodine, sodium, sulfur, phosphorus, docosahexaenoic acid, eicosapentaenoic acid, arachidonic acid, and lutein, and salts, chelates, esters and other derivatives thereof.

The formulations can also include other functional excipients to support the integrity of the dosage form. Thus, in still further subembodiments the formulation further comprises:

a) a bulking agent selected from lactose, sucrose, dextrose, sorbitol, fructose, and cellulose powder;

b) a disintegrating agent selected from microcrystalline cellulose, starches, crospovidone, sodium starch glycolate, and crosscarmellose sodium;

c) a glidant or lubricant selected from talc, corn starch, silicon dioxide, sodium lauryl sulfate, magnesium stearate, calcium stearate, sodium stearate, stearic acid, sodium stearyl fumarate, hydrogenated cotton seed oil, talc, waxes, cetyl alcohol, glyceryl stearate, glyceryl palmitate, glyceryl behenate, hydrogenated vegetable oils, and stearyl alcohol;

d) a taste-masking agent selected from cellulose hydroxypropyl ethers (HPC); low-substituted hydroxypropyl ethers (L-HPC); cellulose hydroxypropyl methyl ethers (HPMC); methylcellulose polymers; Ethylcelluloses (EC) and mixtures thereof; Polyvinyl alcohol (PVA); hydroxyethylcelluloses; carboxymethylcelluloses and salts of carboxymethylcelluloses (CMC); polyvinyl alcohol and polyethylene glycol co-polymers; monoglycerides, triglycerides, polyethylene glycols, modified food starch, acrylic polymers and mixtures of acrylic polymers with cellulose ethers; cellulose acetate phthalate; sepifilms such as mixtures of HPMC and stearic acid, cyclodextrins, and mixtures thereof; and/or e) a flavoring agent selected from acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, or a combination thereof.

The formulation can be present as any suitable oral dosage form, but is preferably a dosage form selected from a tablet, a pill, a soft or hard gelatin capsules, a powder, a granulate, a microsphere, a lozenge, a sachet of packaged powders or granulates or microspheres, an elixir, a suspension, an emulsion, a chewable tablet, or a syrup.

In still another principal embodiment the invention provides an amino acid formulation comprising granulated particles of tyrosine and alginic acid or a pharmaceutically acceptable salt thereof, uncoated by a modified release coating.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Comparative Bioavailability of Amino Acids after Oral Intake of Three Phenylalanine-Free Amino Acid Mixtures—One with a Modified-Release Technology—and Casein Protein as a Positive Control Generic name of the investigational product (Test Product): "APR-1301-01 modified-release amino acid mixture", a modified-release phenylalanine-free synthetic amino acid mixture containing 17 amino acids, carnitine, taurine, vitamins, minerals, other nutrients, and food additives. The modified-release mixture is based on the proprietary technology described herein that provides amino acid modified-release coated granules to be suspended in water.

Study Design:

A four-way, randomized, controlled, single-blind, crossover, single-dose clinical trial in healthy volunteers.

Aim of the Study:

The principal aim of this bioavailability study in healthy volunteers is to demonstrate that the absorption profile of amino acids from the Test Product into the bloodstream is different from that observed with an immediate-release free amino acid mixture (APR-1301-01 immediate-release amino acid mixture) (Reference Product) and tends to be more similar to that of a food protein (Casein), used as a positive control. A marketed phenylalanine-free synthetic amino acid mixture containing amino acids plus vitamins, minerals and other nutrients was used as a reference for a rapid/high absorption of amino acids into the bloodstream.

Primary Objective:

To compare the absorption profile of essential amino acids (EAAs)* after oral intake of the Test Product versus the Reference Product over time. Study hypothesis is that the Test Product reaches statistically significant lower peak plasma concentrations of EAAs and is bioequivalent in terms of area under the concentration-time curve for EAAs during the first 5 hours ($AUC_{0-300\ min}$) in comparison to the Reference Product.

*Essential amino acids: L-histidine, L-isoleucine, L-leucine, L-lysine, L-methionine, L-threonine, L-tryptophan, L-valine, L-arginine, and L-tyrosine. Despite normally not being considered an essential amino acid, tyrosine is included as an EAA in individuals with PKU. Arginine (and tyrosine as well) is added as it is required by infants and growing children. If it is not introduced through diet it will not be available for protein synthesis. Phenylalanine is not counted as it is not contained in APR-1301-01 amino acid mixtures.

Secondary Objectives:
- To compare the absorption profile of large neutral (LNAAs), branched-chain (BCAAs)*, individual** and total amino acids** after oral intake of the Test Product versus the Reference Product, up to 420 min (7 hours).

**LNAAs: L-isoleucine, L-leucine, L-methionine, L-threonine, L-tryptophan, L-valine, L-tyrosine, L-histidine. Phenylalanine is not counted as it is not contained in APR-1301-01 amino acid mixtures.
  ***BCAAs: L-valine, L-leucine, and L-isoleucine. These three amino acids do not undergo first pass metabolism in the liver and thus are most representative of the real absorption of amino acids from the intestine into the bloodstream.
  ****Total amino acids/individual amino acids include 16 (out of 17) amino acids that are contained in the Test Product, the Reference Product and the Product from the market, i.e.: L-histidine, L-isoleucine, L-leucine, L-methionine, L-threonine, L-tryptophan, L-valine, L-lysine, L-tyrosine*, L-arginine**, L-alanine, L-aspartic acid, L-glutamine, glycine, L-proline, and L-serine. L-cystine (the oxidized dimer form of the amino acid cysteine) was not evaluated as it is very instable in plasma samples.

- To compare the Test Product to a Marketed Product and Casein, and to compare the Reference Product to the Marketed Product and Casein, in terms of absorption profile of amino acids (EAAs, LNAAs, BCAAs*, individual** and total amino acids**) up to 420 min, as a secondary statistical analysis.
- To explore additional "efficacy" parameters to evaluate the effects of the different dietary amino acid intakes (Test Product versus Reference Product, Casein and Marketed Product) on the ways amino acids can modify glucose and insulin homeostasis, amino acids are used at tissue levels (anabolic/catabolic pathways).

Study Products & Study Population

The Test Product is a new phenylalanine-free synthetic amino acid mixture containing 17 amino acids plus vitamins, minerals, other nutrients and food additives. It has been developed with the aim of modifying the release of amino acids from the formulation in order to mimic more closely the physiological absorption of amino acids from natural protein intake from food. A modified-release technology allowed the production of amino acid modified-release coated granules to be suspended in water. A manufacturing flow sheet for the Test Product is given as FIG. 1.

The Reference Product is an immediate-release phenylalanine-free amino acid mixture containing 17 amino acids, vitamins, minerals, other nutrients and food additives, like the Test Product.

The Test Product and the Reference Product contain amino acids/vitamins/minerals/other nutrients/food additives in the same qualitative-quantitative composition. The only difference between them is the application of the coating layer in the Test Product that is able to modify the release of amino acids from the formulation and, therefore, the in vivo absorption is expected to be modified.

Positive Control (Casein):

Casein is a milk protein with the ability to form a gel or clot in the stomach. Casein is commonly classified as a slow-release protein, as it is the typical example of a protein that provides a physiological absorption of amino acids into the bloodstream. Food-grade casein (Acid Casein 80 MESH, A.C.E.F., Italy) was chosen as a positive control in this study.

Negative Control (Marketed Product):

A phenylalanine-free synthetic amino acid mixture containing 17 amino acids plus vitamins, minerals and other nutrients, available from the market for the dietary management of subjects with phenylketonuria or hyperphenylalaninemia, was selected. The Marketed Product was chosen among other products available on the market in view of its closer similarity with APR-1301-01 modified-release amino acid mixture in terms of qualitative-quantitative composition of amino acids (especially in terms of EAAs and LNAAs), low content of carbohydrates and absence of fats. It is the reference for a fast absorption of amino acids (with expected high peak concentrations of amino acids) into the bloodstream and acts as a negative control in the study.

The amino acid content in the compositions used in the study is described in Table 1:

TABLE 1

| | Amino Acid Content of Formulations Used in Study | | | | | |
|---|---|---|---|---|---|---|
| | Positive Control | | Test Product | | Marketed Product | |
| amino acids | g amino acids in 100 g of casein | amino acids in 23.8 g of casein | g of amino acids in 100 g of product | amino acids in 32 g powder | g of amino acids in 100 g of product | amino acids in 29.4 g powder |
| Alanine | 2.64 | 0.6283 | 2.250 | 0.7200 | 3.1 | 0.9114 |
| Arginine | 3.26 | 0.7759 | 3.000 | 0.9600 | 2.7 | 0.7938 |
| Aspartic acid | 6.38 | 1.5184 | 4.500 | 1.4400 | 7.6 | 2.2344 |
| Cystine | 0.312 | 0.0743 | 1.500 | 0.4800 | 1.8 | 0.5292 |
| Glutamine | 19.7 | 4.6886 | 15.000 | 4.8000 | 16 | 4.7040 |
| Glycine | 1.7 | 0.4046 | 3.750 | 1.2000 | 1.8 | 0.5292 |
| Histidine | 2.48 | 0.5902 | 2.097 | 0.6710 | 1.8 | 0.5292 |
| Isoleucine | 4.22 | 1.0044 | 4.125 | 1.3200 | 4.5 | 1.3230 |
| Leucine | 8.16 | 1.9421 | 8.625 | 2.7600 | 7.6 | 2.2344 |
| Lysine | 6.89 | 1.6398 | 5.250 | 1.6800 | 5.4 | 1.5876 |
| Methionine | 2.56 | 0.6093 | 1.042 | 0.3334 | 1.8 | 0.5292 |
| Phenylalanine | 4.6 | 1.0948 | 0 | 0.0000 | 0 | 0.0000 |

TABLE 1-continued

Amino Acid Content of Formulations Used in Study

| | Positive Control | | Test Product | | Marketed Product | |
| --- | --- | --- | --- | --- | --- | --- |
| amino acids | g amino acids in 100 g of casein | amino acids in 23.8 g of casein | g of amino acids in 100 g of product | amino acids in 32 g powder | g of amino acids in 100 g of product | amino acids in 29.4 g powder |
| Proline | 9.44 | 2.2467 | 4.500 | 1.4400 | 7.1 | 2.0874 |
| Serine | 5.35 | 1.2733 | 2.542 | 0.8134 | 4 | 1.1760 |
| Threonine | 3.88 | 0.9234 | 3.750 | 1.2000 | 3.6 | 1.0584 |
| Tryptophan | 1.21 | 0.2880 | 1.500 | 0.4800 | 1.4 | 0.4116 |
| Tyrosine | 4.93 | 1.1733 | 7.500 | 2.4000 | 6 | 1.7640 |
| Valine | 5.46 | 1.2995 | 3.750 | 1.2000 | 5.4 | 1.5876 |
| Total | 93.17 | 22.17 | 74.68 | 24.0 | 81.60 | 23.99 |

Number of Subjects (Planned):

32 randomized subjects (16 males+16 females) in order to assure 24 evaluable subjects.

Inclusion Criteria:

Males and females aged 18-45 years (limits included); Weight (kg) within the range of 55-85 kg and body mass index (BMI)≤30 kg/m$^2$; Willing and able to understand and sign the written informed consent form; Willing to consume medical nutrition products, specifically amino acid preparations (L-amino acids/protein substitutes), and to follow the dietary scheme as required by the protocol; Good general health status, as documented by normal findings in the medical history, physical examination, 12-lead ECG, vital signs (body temperature, systolic and diastolic blood pressure, heart rate after a 3-min rest), laboratory parameters. Values for the laboratory parameters will be compared with normal ranges from the laboratory. Parameters out of these normal ranges will be carefully evaluated by the Investigator who will decide whether to consider them "clinically not relevant" or "clinically relevant" for the current study; Non-smokers or not current smokers.

Doses of Study Products:

Each study product will be administered in single dose, orally. For the three amino acid mixtures (Test Product, Reference Product and Marketed Product), the total amount of amino acids will be of 0.4 g amino acid/kg body weight. Doses of each study product (grams of product to give) will be calculated on the basis of the total grams of amino acids (or protein, for casein)/100 grams of each finished product and the subject's body weight.

Subjects will be divided in 3 weight & energy categories as follows: 55-65.4 kg body weight—24 g amino acids (dose) equals to 20.0 g protein equivalents; 65.5-75.4 kg body weight—28 g amino acids (dose) equals to 23.3 g protein equivalents; 75.5-85 kg body weight—32 g amino acids (dose) equals to 26.6 g protein equivalents.

Study Description

In addition to the screening visit, the trial will consist of 4 study visits corresponding to 4 test days (Test Day 1, Test Day 2, Test Day 3, and Test Day 4) in which the study products are given to subjects in a randomized order. A total of 3 washout periods are foreseen: between Test Day 1 and Test Day 2 (Washout 1), between Test Day 2 and Test Day 3 (Washout 2), and between Test Day 3 and Test Day 4 (Washout 3). Each washout period will last from a minimum of 9 days to a maximum of 14 days. The total duration of the study for each subject will be of approximately 38-70 days (including 7-14 days of screening period, 4 test days, 3 washout periods each lasting 9-14 days, and the follow-up visit after a few days from the last study visit, in case it is required). The total amount of blood taken during the whole trial from each subject will be of 475 mL, including the screening visit, corresponding to the typical amount of blood taken during a blood donation.

Study Endpoints

Primary Kinetic Endpoints:

Rate of absorption (i.e. $C_{max}$) of EAAs after oral intake of the Test Product versus the Reference Product to demonstrate that the $C_{max}$ of EAAs from the Test Product is statistically significantly inferior to that from the Reference Product of at least 20%. If the above primary hypothesis is reached, further analysis will be performed to demonstrate that the Test Product is at least equivalent (equivalent or superior) to the Reference Product in terms of extent of absorption during the first 5 hours after the intake ($AUC_{0-300\ min}$) for EAAs. Thus, $AUC_{0-300\ min}$ has to be within the bioequivalence range (or out for the upper limit). Thus, ln-transformed $AUC_{0-300\ min}$ ratio should produce 90% confidence intervals (CIs) in the range 0.80-1.25 (or >1.25).

Secondary Kinetic Endpoints:

$C_{max}$ of LNAAs, BCAAs, total amino acids and individual amino acids after oral intake of the Test Product versus the Reference Product; $AUC_{0-300\ min}$ of LNAAs, BCAAs, total amino acids and individual amino acids after oral intake of the Test Product versus the Reference Product; $AUC_{0-150\ min}$; $AUC_{150-300\ min}$; $AUC_{300-420\ min}$ and $AUC_{0-420\ min}$ of EAAs, LNAAs, BCAAs, total amino acids and individual amino acids after oral intake of the Test Product versus the Reference Product; Time to peak ($t_{max}$), of EAAs, LNAAs, BCAAs, total amino acids and individual amino acids after oral intake of the Test Product versus the Reference Product; Plasma concentration at the last evaluable time point before the snack meal ($C_{300\ min}$) and at the last evaluable time point after the snack meal ($C_{420\ min}$) of EAAs, LNAAs, BCAAs, total amino acids and individual amino acids after oral intake of the Test Product versus the Reference Product.

The comparison between the Test Product and the Reference Product will represent the primary comparison, from a statistical point of view.

As a secondary statistical analysis, $C_{max}$, AUCs ($AUC_{0-150\ min}$, $AUC_{0-300\ min}$, $AUC_{0-420\ min}$, $AUC_{150-300\ min}$, $AUC_{300-420\ min}$), $t_{max}$, $C_{300\ min}$ and $C_{420\ min}$ of EAAs, LNAAs, BCAAs, total amino acids and individual amino acids after oral intake of: the Test Product versus the Marketed Product and Casein; the Reference Product versus the Marketed Product and Casein.

Other Secondary Endpoints:

Comparison of the levels of "efficacy" parameters—glucose, insulin, ghrelin, blood urea nitrogen (BUN) and urea at specific time points after oral intake of the Test Product versus the Reference Product, the Marketed and Casein. These parameters allow measure the effects of the different dietary intakes on the ways amino acids can modify glucose and insulin homeostasis, amino acids are used at tissue levels (anabolic/catabolic pathways) or on the satiety hormone (ghrelin, as "optional" analysis).

Safety and Tolerability:

Safety and tolerability will be monitored throughout the whole duration of the study.

Study Results

Subject Disposition:

TABLE 2

| Screened and Randomized Subjects | |
|---|---|
| Screened subjects | 43 |
| Screening-failure subjects | 8 |
| Randomized subjects | 35 |
| Drop-out subjects | 4 |
| Subjects with major protocol deviations | 3 |

TABLE 3

| PP Population | | | |
|---|---|---|---|
| Test Product | Reference Product | Marketed Product | Casein |
| 28 | 30 | 29 | 30 |

Results:

For all the amino acid subgroups (EAAs, LNAAs, BCAAs and total AAs), the Test Product produced a lower $C_{max}$ than the Reference Product. In terms of AUCs, $AUC_{0-7h}$ were fully in the range of bioequivalence for EAAs, LNAAs, BCAAs and total AAs. The administration of the Test Product relative to the administration of the Reference Product yielded:

More stable Tyrosine bioavailability

Phenylalanine appeared more stable and with smaller fluctuations

Lower insulin peak with more stable levels of glucose in the blood

Lower Blood urea nitrogen (BUN) and urea levels

The results of the study are reported in FIGS. 2-12 and Tables 4-13.

TABLE 4

Primary endpoints: $C_{max}$ & $AUC_{0-300\ min}$ of EAAs

| | Test Product | Reference Product | Ratio of geometric LSM Estimate (95% CI) | p value |
|---|---|---|---|---|
| $C_{max}$ (µM) | | | | |
| Mean (SD) | 1768.2 (252.77) | 2434.6 (367.52) | 0.726 (0.690, 0.764) | <0.0001 |
| CV (%) | 14.3 | 15.1 | | |
| $AUC_{0-300\ min}$ (µmol/L * min) | | | | |
| Mean (SD) | 396027.6 (44935.44) | 443869.8 (46190.52) | 0.890 (0.865, 0.915) | — |
| CV (%) | 11.3 | 10.4 | | |

TABLE 5

Secondary kinetic endpoints: $AUC_{0-420\ min}$, $C_{last}$ & $t_{max}$ of EAAs

| | Test Product | Reference Product | Ratio of geometric LSM Estimate (95% CI) | p value |
|---|---|---|---|---|
| $AUC_{0-420\ min}$ | | | | |
| Mean (SD) | 508855.6 (57172.36) | 549374.1 (55167.22) | 0.924 (0.900, 0.950) | — |
| CV (%) | 11.2 | 10.0 | | |
| $C_{300\ min}$ (µM) | | | | |
| Mean (SD) | 1064.6 (124.16) | 995.8 (116.70) | 1.074 (1.030-1.120) | 0.0012 |
| $C_{420\ min}$ (µM) | | | | |
| Mean (SD) | 822.7 (119.92) | 780.1 (88.16) | 1.054 (1.010-1.100) | 0.0158 |
| $t_{max}$ (min) | | | | |
| Mean (SD) | 62.2 (19.45) | 65.5 (16.47) | — | NS |

TABLE 6

Secondary kinetic endpoints: LNAAs

| | Test Product | Reference Product | Ratio of geometric LSM Estimate (95% CI) | p value |
|---|---|---|---|---|
| $C_{max}$ (µM) | | | | |
| Mean (SD) | 1265.3 (175.15) | 1872.4 (301.08) | 0.677 (0.644, 0.713) | <0.0001 |
| CV (%) | 13.8 | 16.1 | | |
| $AUC_{0\text{-}300\ min}$ | | | | |
| Mean (SD) | 297480.6 (33837.62) | 341853.2 (37142.16) | 0.869 (0.846, 0.892) | — |
| CV (%) | 11.4 | 10.9 | | |
| $AUC_{0\text{-}420\ min}$ | | | | |
| Mean (SD) | 385042.3 (43215.11) | 423787.3 (43934.14) | 0.908 (0.885, 0.932) | — |
| CV (%) | 11.2 | 10.4 | | |
| $C_{300\ min}$ (µM) | | | | |
| Mean (SD) | 830.6 (97.47) | 776.9 (92.41) | 1.074 (1.029-1.121) | 0.0013 |
| $C_{420\ min}$ (µM) | | | | |
| Mean (SD) | 628.3 (92.01) | 595.1 (67.72) | 1.055 (1.012-1.101) | 0.0123 |
| $t_{max}$ (min) | | | | |
| Mean (SD) | 65.9 (27.78) | 67.0 (16.59) | — | NS |

TABLE 7

Secondary kinetic endpoints: BCAAs

| | Test Product | Reference Product | Ratio of geometric LSM Estimate (95% CI) | p value |
|---|---|---|---|---|
| $C_{max}$ (µM) | | | | |
| Mean (SD) | 692.8 (106.48) | 1201.1 (221.18) | 0.579 (0.547, 0.612) | <0.0001 |
| CV (%) | 15.4 | 18.4 | | |
| $AUC_{0\text{-}300\ min}$ | | | | |
| Mean (SD) | 160355.2 (22144.57) | 198816.3 (24494.06) | 0.803 (0.780, 0.827) | — |
| CV (%) | 13.8 | 12.3 | | |
| $AUC_{0\text{-}420\ min}$ | | | | |
| Mean (SD) | 206603.5 (28352.92) | 239573.9 (29549.71) | 0.860 (0.836, 0.885) | — |
| CV (%) | 13.7 | 12.3 | | |
| $C_{300\ min}$ (µM) | | | | |
| Mean (SD) | 458.4 (63.81) | 402.9 (60.72) | 1.144 (1.089-1.203) | <0.0001 |
| $C_{420\ min}$ (µM) | | | | |
| Mean (SD) | 316.1 (59.56) | 281.5 (52.47) | 1.126 (1.076-1.179) | <0.0001 |
| $t_{max}$ (min) | | | | |
| Mean (SD) | 60.6 (28.72) | 65.5 (17.83) | — | NS |

TABLE 8

Secondary kinetic endpoints: total amino acids

|  | Test Product | Reference Product | Ratio of geometric LSM Estimate (95% CI) | p value |
|---|---|---|---|---|
| $C_{max}$ (μM) | | | | |
| Mean (SD) | 3566.5 (468.10) | 4586.6 (575.72) | 0.775 | <0.0001 |
| CV (%) | 13.1 | 12.6 | (0.737, 0.815) | |
| $AUC_{0\text{-}300\ min}$ | | | | |
| Mean (SD) | 839146.2 (99093.97) | 914613.4 (75479.35) | 0.913 | — |
| CV (%) | 11.8 | 8.3 | (0.885, 0.941) | |
| $AUC_{0\text{-}420\ min}$ | | | | |
| Mean (SD) | 1106090.3 (129426.51) | 1176026.8 (97284.78) | 0.937 | — |
| CV (%) | 11.7 | 8.3 | (0.909, 0.966) | |
| $C_{300\ min}$ (μM) | | | | |
| Mean (SD) | 2330.6 (284.99) | 2260.8 (232.47) | 1.034 (0.992-1.078) | NS |
| $C_{420\ min}$ (μM) | | | | |
| Mean (SD) | 2084.5 (275.24) | 2060.0 (206.75) | 1.012 (0.970-1.057) | NS |
| $t_{max}$ (min) | | | | |
| Mean (SD) | 63.8 (19.84) | 67.5 (15.08) | — | NS |

TABLE 9

Secondary kinetic endpoints: Tyrosine

|  | Test Product | Reference Product | Ratio of geometric LSM Estimate (95% CI) | p value |
|---|---|---|---|---|
| $C_{max}$ (μM) | | | | |
| Mean (SD) | 124.9 (32.70) | 119.1 (33.15) | 1.058 | NS |
| CV (%) | 26.2 | 27.8 | (0.969, 1.155) | |
| $AUC_{0\text{-}300\ min}$ | | | | |
| Mean (SD) | 29245.8 (6783.61) | 27015.6 (6747.26) | 1.094 | — |
| CV (%) | 23.2 | 25.0 | (1.015, 1.178) | |
| $AUC_{0\text{-}420\ min}$ | | | | |
| Mean (SD) | 37492.3 (8446.50) | 35880.0 (8371.14) | 1.052 | — |
| CV (%) | 22.5 | 23.3 | (0.984, 1.125) | |
| $C_{300\ min}$ (μM) | | | | |
| Mean (SD) | 83.0 (21.77) | 88.2 (25.72) | 0.95 (0.866-1.042) | NS |
| $C_{420\ min}$ (μM) | | | | |
| Mean (SD) | 55.2 (12.67) | 60.7 (15.01) | 0.917 (0.848-0.991) | 0.0291 |
| $t_{max}$ (min) | | | | |
| Mean (SD) | 113.6 (63.93) | 182.7 (92.16) | — | 0.0036 |

TABLE 10

Secondary "safety" endpoints: phenylalanine

| | Test Product | Reference Product | Ratio of geometric LSM Estimate (95% CI) | p value |
|---|---|---|---|---|
| $C_{min}$ (μM) | | | | |
| Mean (SD) | 24.8 (8.73) | 17.2 (6.54) | — | — |
| CV (%) | 35.2 | 38 | | |
| $AUC_{0\text{-}300\ min}$ | | | | |
| Mean (SD) | 10176.2 (2351.84) | 8474.6 (1863.71) | 1.203 (1.118, 1.294) | — |
| CV (%) | 23.1 | 22.0 | | |
| $AUC_{0\text{-}420\ min}$ | | | | |
| Mean (SD) | 13683.2 (3434.16) | 11984.9 (2666.25) | 1.143 (1.060, 1.232) | — |
| CV (%) | 25.1 | 22.2 | | |
| $C_{150\ min}$ (μM) | | | | |
| Mean (SD) | 28.2 (8.74) | 18.5 (6.99) | 1.059 (0.950-1.180) | — |
| $C_{300\ min}$ (μM) | | | | |
| Mean (SD) | 28.4 (10.02) | 26.6 (7.00) | 0.939 (0.863-1.022) | NS |
| $C_{420\ min}$ (μM) | | | | |
| Mean (SD) | 31.0 (9.51) | 32.7 (7.32) | | NS |

TABLE 11

Secondary "efficacy" endpoints: insulin

| | Test Product | Reference Product | Ratio of geometric LSM Estimate (95% CI) | p-value |
|---|---|---|---|---|
| $AUC_{0\text{-}300\ min}$ (mU/L * min) | | | | |
| Mean (SD) | 2137.9 (1011.68) | 2703.7 (1375.05) | 0.785 (0.716-0.861) | — |
| CV (%) | 47.3 | 50.9 | | |

TABLE 12

Secondary "efficacy" endpoints: glucose

| | Test Product | Reference Product | Ratio of geometric LSM Estimate (95% CI) | p-value |
|---|---|---|---|---|
| $AUC_{0\text{-}300\ min}$ (mmol/L * min) | | | | |
| Mean (SD) | 1621.2 (91.49) | 1609.4 (93.35) | 1.005 (0.992-1.019) | — |
| CV (%) | 5.6 | 5.8 | | |

TABLE 13

Secondary "efficacy" endpoints: BUN & urea

| | Test Product | Reference Product | Ratio of geometric LSM Estimate (95% CI) | p-value |
|---|---|---|---|---|
| $AUC_{0\text{-}300\ min}$ BUN (mmol/L * min) | | | | |
| Mean (SD) | 1357.4 (201.24) | 1572.9 (265.88) | 0.868 (0.837-0.900) | — |
| CV (%) | 14.8 | 16.9 | | |

TABLE 13-continued

Secondary "efficacy" endpoints: BUN & urea

| | Test Product | Reference Product | Ratio of geometric LSM Estimate (95% CI) | p-value |
|---|---|---|---|---|
| $AUC_{0-300\ min}$ urea (mU/L * min) | | | | |
| Mean (SD) | 53207.1 (24902.23) | 69467.5 (28999.71) | 0.767 | — |
| CV (%) | 46.8 | 41.7 | (0.684-0.860) | |

Example 2. Quali-Quantitative Formulation and List of Ingredients Related to the Test Product Used in the Human PK Trial (Example 1)

TABLE 14

Complete Listing of Ingredients of Test Product used in Human PK Trial

| | | Ingredient | g for 100 g of finished product |
|---|---|---|---|
| GRANULES | Coated granules | L-Glutamine | 15.0000 |
| | | L-Leucine | 8.6250 |
| | | L-Lysine | 5.2500 |
| | | L-Aspartic Acid | 4.5000 |
| | | L-Proline | 4.5000 |
| | | L-Isoleucine | 4.1250 |
| | | L-Threonine | 3.7500 |
| | | Glicine | 3.7500 |
| | | L-Valine | 3.7500 |
| | | L-Arginine | 3.0000 |
| | | L-Serine | 2.5417 |
| | | L-Alanine | 2.2500 |
| | | L-Histidine | 2.0967 |
| | | L-Cystine | 1.5000 |
| | | L-Tryptophan | 1.5000 |
| | | L-Methionine | 1.0417 |
| | | Taurine | 0.2083 |
| | | L-Carnitine | 0.0833 |
| | | Sodium Alginate | 0.0542 |
| | | Ethylcellulose | 6.9659 |
| | Uncoated granules | L-Tyrosine | 7.5000 |
| | | Sodium Alginate | 0.1923 |
| EXTRA GRANULES (Source of Vitamins, minerals and other elements) | | Calcium hydrogen phosphate dihydrate E 341 (ii) (Ca 23.30%; P18.10%) | 5.7480150 |
| | | Maltodextrin pineflow (Tapioca starch) | 4.6186617 |
| | | Potassium bicarbonate E 501 (ii) | 3.2010243 |
| | | Choline bitartrate | 0.7814653 |
| | | Magnesium oxide (PLV PESANTE E530) | 0.5059514 |
| | | Inositol | 0.2142875 |
| | | Ferrous gluconate 11.3% | 0.2054204 |
| | | Vitamin C - L-ascorbic acid E 300 | 0.1749908 |
| | | Zinc sulphate heptahydrate | 0.0628298 |
| | | Vitamin PP (B3) - nicotinamide - niacin | 0.0348238 |
| | | Vitamin E acetate (alfa tocopherol equivalents 67%) liquid | 0.0261213 |
| | | Chromium chloride hexahydrate 1% maltodextrin | 0.0235043 |
| | | Sodium molybdate 1% | 0.0220681 |
| | | Manganese gluconate | 0.0204082 |
| | | Vitamin B5 - calcium pantothenate (pantothenic acid 92.10%) | 0.0151208 |
| | | Copper gluconate (copper 14%) | 0.0102083 |
| | | Vitamin A palmitate (retinol) | 0.0056153 |
| | | Vitamin B6 - pyridoxine hydrochloride | 0.0040887 |
| | | Vitamin B1 hydrochloride - thiamine | 0.0032430 |
| | | Vitamin B2 - riboflavin titration 100% | 0.0024592 |
| | | Vitamin D3 - cholecalciferol - 1.0 million UI/g (2.5%) liquid | 0.0013000 |
| | | Folic acid (pteroyl glutamicacid) | 0.0003467 |
| | | Potassium iodide | 0.0002945 |

TABLE 14-continued

Complete Listing of Ingredients of Test Product used in Human PK Trial

| Ingredient | g for 100 g of finished product |
|---|---|
| Vitamin K1 - fitomenadione | 0.0001300 |
| Sodium selenite | 0.0001296 |
| Vitamin H (B8) - biotin | 0.0000704 |
| Vitamin B12 - cyanocobalamin | 0.0000054 |

List of Ingredients: L-glutamine, L-leucine, ethylcellulose, L-tyrosine, L-lysine Acetate, calcium hydrogen phosphate dihydrate, L-aspartic acid, L-proline, L-isoleucine, maltodextrin, L-threonine, L-glycine, L-valine, potassium bicarbonate, L-arginine, L-histidine, L-serine, L-alanine, L-cystine, L-tryptophan, L-methionine, choline bitartrate, magnesium oxide, sodium alginate, inositol, L-taurine, ferrous gluconate, L-ascorbic acid—vitamin, L-carnitine, zinc sulphate heptahydrate, vitamin PP (B3)—nicotinamide—niacin, vitamin E acetate, chromium chloride hexahydrate, sodium molybdate, manganese gluconate, vitamin B5—calcium pantothenate, copper gluconate, vitamin A palmitate (retinyl palmitate), vitamin B6, pyridoxine hydrochloride, vitamin B1 hydrochloride (thiamine), vitamin B2, vitamin D3—cholecalciferol, folic acid, potassium iodide, vitamin K1—fitomenadione, sodium selenite, vitamin H (B8)—biotin, vitamin B12—cyanocobalamin

Example 3. Dissolution Pests on Test and Reference Products Used in Human PK Trial Ponderal Dissolution Profile The aim of the ponderal dissolution method is the quantification of the total amount of dissolved amino acids at each time points. The percentage release obtained represents the summation of all the dissolved amino acids.
Analytical Conditions
Dissolution Medium: Medium pH 1.2±0.1 (0.1N Hydrochloric acid: 8.3 mL/L)
Apparatus: Paddle (Apparatus 2, USP <711>); 50 rpm, gentle mix at start
Temperature: 37±0.5° C.
Volume Medium: 500 mL
Sample: 2.0 g of Amino Acid Each time point has its own dissolution vessel. At the stated sampling times, samples are filtered; remaining powder and filter are dried for ±4 hours in vacuum oven at 50° C. until constant weight. Samples are weighed and the undissolved amino acid percentage calculated. Ponderal dissolution test results for the Reference and Test Products are plotted in FIGS. 13 and 14, respectively.
Dissolution Profile: Single Amino Acids The aim of the single amino acid dissolution method is the quantification of the dissolved amount of each amino acid at the stated time points
Analytical Conditions
Dissolution Medium: Medium pH 1.2±0.1 (0.1N Hydrochloric acid: 8.3 mL/L)
Apparatus: Paddle (Apparatus 2, USP <711>); 50 rpm, gentle mix at start
Temperature: 37±0.5° C.
Volume Medium: 500 mL
Sample: 2.0 g of Amino Acid Aliquots collected from the dissolution medium, are analyzed by High Performance Liquid Chromatography (HPLC) with Fluorimetric Detector, exception done for carnitine that is analyzed by Liquid Chromatography coupled with Mass Spectrometry (LC/MS).

By evaluating the concentrations of each amino acid in the dissolution medium, the release profile is calculated. Individual amino acid dissolution test results for the Reference and Test Products are plotted in FIGS. 15 and 16, respectively.

Example 4. Effect of Chronic Administration of Amino Acids Formulated Using Modified Release Technology The study was performed in two consecutive in-vivo phases. Healthy Wistar rats, 7/8 weeks of age, were fed from day 1 to day 15 (16 days) two gavages per day covering in total the protein need of 2.5 g per Kg of body weight (calculated as 5% of protein need on 50 g/Kg body weight of maintenance diet). The composition of each gavage was: 1.694 g/Kg bw of Test Formulation or Placebo Formulation, 0.35 mg/Kg bw of free phenylalanine, glucose 5%, starch 5%, and mineral supplements. Beside the gavages, the groups were fed with a feed including all the nutrients of a normal diet for rats, except for nitrogen source. This feed was ad libitum except for two hours before and after each gavage.

The compared groups were:

Test Formulation (Amino Acids formulated with modified-release technology):

| Ingredient | g in 100 g |
|---|---|
| L-Glutamine | 17.7899 |
| L-Leucine | 10.2292 |
| L-Lysine | 6.2084 |
| L-Aspartic Acid | 5.3370 |
| L-Proline | 5.3370 |
| L-Isoleucine | 4.8922 |
| L-Threonine | 4.4475 |
| Glycine | 4.4475 |
| L-Valine | 4.4475 |
| L-Arginine | 3.5580 |
| L-Histidine | 2.4866 |
| L-Serine | 3.0144 |
| L-Alanine | 2.6685 |
| L-Cystine | 1.7790 |
| L-Tryptophan | 1.7790 |
| L-Methionine | 1.2354 |
| Taurine | 0.2471 |
| L-Carnitine | 0.0988 |
| L-Tyrosine | 8.8950 |
| Sodium alginate | 0.2922 |
| Ethyl Cellulose | 8.2600 |

Placebo Formulation (same quali-quantitative composition as the Test Formulation without the modified release technology applied)

Effect of Treatment on Muscle Strength

The muscle strength of animals treated with Test and Placebo Formulations was measured by a standard GRIP meter. The index of strength was calculated as "GRIP value/body weight" and it was observed to be significantly increased in the Test group after 15 days of treatment versus baseline. The same was not observed for the Placebo group. Results are reported in Table and FIG. 17.

TABLE 15

Unpaired T test

| | |
|---|---|
| Test Formulation vs baseline | 0.0092 |
| Placebo Formulation vs baseline | ns |

The average percentage of strength increase of each animal observed at the end of treatment versus T0 is about 30% in the Test group compared to about 13% in the Placebo group.

Western Blot Analysis

The ability of the Test formulation to slow protein degradation (proteolysis) was investigated directly by Western blot for the ubiquitin-mediated proteolysis pathways, including MAFbx/Atrogin-1, and mitochondrial BNIP3L in skeletal muscle biopsies after 15 days of treatment. Protein synthesis was measured in the same muscle samples. Mechanistic target of rapamycin (mTOR) pathway that is involved in protein synthesis induced mainly by leucine, as well as myostatin, (protein regulating muscle growth), was studied by immunoblot analysis with specific antibodies.

Nix (also called Bnip3L) is implicated in both apoptosis and mitophagy. These cytoplasmatic proteins translocate to mitochondria, form homodimers and disrupt mitochondrial membrane potential. In skeletal muscle, mitochondrial dysfunction caused by the transient overexpression of Nix triggers autophagy and induces muscle atrophy.

Nix expression in the femoral biceps measured by Western Blot was significantly lower after Test formulation administration than after Placebo administration. See FIG. 18 (Unpaired t test, p=0,0239). The same trend could be observed in the vastus lateralis muscles. Based on these results it can be concluded that the Test formulations, thanks to their extended release profile, prevent muscle proteolysis.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating muscle proteolysis manifesting as weight or muscle loss or elevated blood urea nitrogen (BUN) or urea concentrations in a subject in need thereof, the method comprising administering to the subject a therapeutically effective amount of a modified release amino acid formulation comprising a plurality of modified release granules, the plurality of modified release granules comprising:

a) a sodium alginate binder admixed with an amino acid component comprising alanine, arginine, aspartic acid, cystine, glutamine, glycine, histidine, isoleucine, leucine, lysine, methionine, proline, serine, threonine, tryptophan, and valine; and b) an ethylcellulose coating layer that coats each modified release granule; and wherein no more than 70% of the amino acids in the plurality of modified release granules in the formulation are released after 30 minutes when 2 g of the formulation is subjected to dissolution testing in a <711> USP 39 NF 34 paddle apparatus at 37° C. in 500 ml 0.1 N hydrochloric acid at a paddle speed of 50 rpm, further wherein the alanine comprises about 3 wt % of the modified release granule;

the arginine comprises about 4 wt % of the modified release granule;

the aspartic acid comprises about 6 wt % of the modified release granule;

the cystine comprises about 2 wt % of the modified release granule;

the glutamine comprises about 20 wt % of the modified release granule;

the glycine comprises about 5 wt % of the modified release granule;

the histidine comprises about 2.8 wt % of the modified release granule;

the isoleucine comprises about 5.5 wt % of the modified release granule;

the leucine comprises about 11.5 wt % of the modified release granule;

the lysine comprises about 7 wt % of the modified release granule;

the methionine comprises about 1.4 wt % of the modified release granule;

the proline comprises about 6 wt % of the modified release granule;

the serine comprises about 3.4 wt % of the modified release granule;

the threonine comprises about 5 wt % of the modified release granule;

the tryptophan comprises about 2 wt % of the modified release granule; and the valine comprises about 5 wt % of the modified release granule.

2. The method of claim 1, wherein the subject is suffering from tyrosinemia.

3. The method of claim 1, wherein the formulation provides a total amino acid maximum plasma concentration of less than 80% of the maximum plasma concentration produced by an equipotent immediate release amino acid formulation.

4. The method of claim 1, wherein the formulation provides a total amino acid AUC that is greater 90% of the AUC produced by an equipotent immediate release amino acid formulation.

5. The method of claim 1, wherein the formulation further comprises carnitine, taurine, or a combination thereof.

6. The method of claim 1, wherein the formulation further comprises one or more additional ingredients selected from the group consisting of: vitamins, minerals, carbohydrates, choline, inositol, vitamin A, vitamin D, vitamin E, vitamin K, vitamin C, thiamin, riboflavin, niacin, vitamin B6, folate, vitamin B12, biotin, pantothenic acid, potassium, calcium, magnesium, iron, zinc, copper, manganese, selenium, chromium, molybdenum, iodine, sodium, sulfur, phosphorus, docosahexaenoic acid, eicosapentaenoic acid, arachidonic acid, lutein, salts thereof, chelates thereof, esters thereof, and derivatives thereof.

7. The method of claim 1, wherein the formulation further comprises one or more additional ingredients selected from the group consisting of:
   a. a bulking agent selected from lactose, sucrose, dextrose, sorbitol, fructose, and cellulose powder;
   b. a disintegrating agent selected from microcrystalline cellulose, starches, crospovidone, sodium starch glycolate, and crosscarmellose sodium;
   c. a glidant or lubricant selected from talc, corn starch, silicon dioxide, sodium lauryl sulfate, magnesium stearate, calcium stearate, sodium stearate, stearic acid, sodium stearyl fumarate, hydrogenated cotton seed oil, talc, waxes, cetyl alcohol, glyceryl stearate, glyceryl palmitate, glyceryl behenate, hydrogenated vegetable oils, and stearyl alcohol;
   d. a taste-masking agent selected from cellulose hydroxypropyl ethers (HPC), low substituted hydroxypropyl ethers (L-HPC), cellulose hydroxypropyl methyl ethers (HPMC), methylcellulose, ethylcelluloses (EC), hydroxyethylcelluloses, carboxymethylcelluloses (CMC), salts of carboxymethylcelluloses, polyvinyl alcohol (PVA), polyethylene glycols, copolymers of polyvinyl alcohol and polyethylene glycol, monoglycerides, triglycerides, modified food starch, acrylic polymers, mixtures of acrylic polymers with cellulose ethers, cellulose acetate phthalate, mixtures of HPMC and stearic acid, cyclodextrins, and mixtures thereof; and
   e. a flavoring agent selected from acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, and a combination thereof.

8. The method of claim 1, wherein the formulation is in the form of a medical food, a tablet, a pill, a soft gelatin capsule, a hard gelatin capsule, a powder, a granulate, a microsphere, a lozenge, a sachet of packaged powders, a sachet of packaged granulates, a sachet of packaged microspheres, an elixir, a suspension, an emulsion, a chewable tablet, or a syrup.

9. The method of claim 1, wherein the formulation further comprises a plurality of tyrosine-containing granules comprising tyrosine and a second binder.

10. The method of claim 9, wherein the tyrosine comprises about 97 wt % of the plurality of tyrosine-containing granules.

11. The method of claim 9, wherein the alanine comprises about 2.67 wt % of the total formulation;

the arginine comprises about 3.56 wt % of the total formulation;
the aspartic acid comprises about 5.34 wt % of the total formulation;
the cystine comprises about 1.78 wt % of the total formulation;
the glutamine comprises about 17.79 wt % of the total formulation;
the glycine comprises 4.45 wt % of the total formulation;
the histidine comprises about 2.49 wt % of the total formulation;
the isoleucine comprises about 4.9 wt % of the total formulation;
the leucine comprises about 10.23 wt % of the total formulation;
the lysine comprises about 6.21 wt % of the total formulation;
the methionine comprises about 1.24 wt % of the total formulation;
the proline comprises 5.34 wt % of the total formulation;
the serine comprises about 3 wt % of the total formulation;
the threonine comprises about 4.45 wt % of the total formulation;
the tryptophan comprises about 1.8 wt % of the total formulation;
the tyrosine comprises about 8.9 wt % of the total formulation; and
the valine comprises about 4.45 wt % of the total formulation.

12. The method of claim 9, wherein the subject is suffering from phenylketonuria (PKU).

13. The method of claim 12, wherein the subject has mild PKU, defined as a phenylalanine concentration of from 600 to 1200 micromole/L (from 10 to 20 mg/dL), and the modified release amino acid formulation lacks phenylalanine.

14. The method of claim 9, wherein the second binder comprises alginic acid or a salt thereof.

15. The method of claim 14, wherein the second binder is sodium alginate.

16. The method of claim 9, wherein the formulation provides a total amino acid maximum plasma concentration of less than 80% of the maximum plasma concentration produced by an equipotent immediate release amino acid formulation.

17. The method of claim 9, wherein the formulation provides a total amino acid AUC that is greater 90% of the AUC produced by an equipotent immediate release amino acid formulation.

18. The method of claim 9, wherein the formulation further comprises carnitine, taurine, or a combination thereof.

19. The method of claim 9, wherein the formulation further comprises one or more additional ingredients selected from the group consisting of: vitamins, minerals, carbohydrates, choline, inositol, vitamin A, vitamin D, vitamin E, vitamin K, vitamin C, thiamin, riboflavin, niacin, vitamin B6, folate, vitamin B12, biotin, pantothenic acid, potassium, calcium, magnesium, iron, zinc, copper, manganese, selenium, chromium, molybdenum, iodine, sodium, sulfur, phosphorus, docosahexaenoic acid, eicosapentaenoic acid, arachidonic acid, lutein, salts thereof, chelates thereof, esters thereof, and derivatives thereof.

20. The method of claim 9, wherein the formulation further comprises one or more additional ingredients selected from the group consisting of:

a. a bulking agent selected from lactose, sucrose, dextrose, sorbitol, fructose, and cellulose powder;
b. a disintegrating agent selected from microcrystalline cellulose, starches, crospovidone, sodium starch glycolate, and crosscarmellose sodium;
c. a glidant or lubricant selected from talc, corn starch, silicon dioxide, sodium lauryl sulfate, magnesium stearate, calcium stearate, sodium stearate, stearic acid, sodium stearyl fumarate, hydrogenated cotton seed oil, talc, waxes, cetyl alcohol, glyceryl stearate, glyceryl palmitate, glyceryl behenate, hydrogenated vegetable oils, and stearyl alcohol;
d. a taste-masking agent selected from cellulose hydroxypropyl ethers (HPC), low substituted hydroxypropyl ethers (L-HPC), cellulose hydroxypropyl methyl ethers (HPMC), methylcellulose, ethylcelluloses (EC), hydroxyethylcelluloses, carboxymethylcelluloses (CMC), salts of carboxymethylcelluloses, polyvinyl alcohol (PVA), polyethylene glycols, copolymers of polyvinyl alcohol and polyethylene glycol, monoglycerides, triglycerides, modified food starch, acrylic polymers, mixtures of acrylic polymers with cellulose ethers, cellulose acetate phthalate, mixtures of HPMC and stearic acid, cyclodextrins, and mixtures thereof; and
e. a flavoring agent selected from acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, and a combination thereof.

21. The method of claim 9, wherein the formulation is in the form of a medical food, a tablet, a pill, a soft gelatin capsule, a hard gelatin capsule, a powder, a granulate, a microsphere, a lozenge, a sachet of packaged powders, a sachet of packaged granulates, a sachet of packaged microspheres, an elixir, a suspension, an emulsion, a chewable tablet, or a syrup.

* * * * *